US012691263B2

(12) United States Patent
Nakajima et al.

(10) Patent No.: US 12,691,263 B2
(45) Date of Patent: Jul. 28, 2026

(54) MEDICAL BALLOON CATHETER AND MANUFACTURING METHOD OF MEDICAL BALLOON CATHETER

(71) Applicant: OLYMPUS CORPORATION, Tokyo (JP)

(72) Inventors: Takahito Nakajima, Hachioji (JP); Junichi Sato, Tokyo (JP); Yasunori Oki, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 939 days.

(21) Appl. No.: 17/890,552

(22) Filed: Aug. 18, 2022

(65) Prior Publication Data

US 2022/0401708 A1     Dec. 22, 2022

Related U.S. Application Data

(63) Continuation of application No. PCT/JP2020/008008, filed on Feb. 27, 2020.

(51) Int. Cl.
*A61M 25/10*     (2013.01)
*A61M 25/00*     (2006.01)
*A61M 25/09*     (2006.01)

(52) U.S. Cl.
CPC .... *A61M 25/1025* (2013.01); *A61M 25/0026* (2013.01); *A61M 25/09* (2013.01); *A61M 2025/1061* (2013.01); *A61M 2207/10* (2013.01)

(58) Field of Classification Search
CPC ........ A61M 25/104; A61M 2025/1061; A61M 25/1025; A61M 2025/1056
See application file for complete search history.

(56) References Cited

U.S. PATENT DOCUMENTS

| | | | |
|---|---|---|---|
| 4,782,834 A | 11/1988 | Maguire et al. | |
| 5,769,814 A * | 6/1998 | Wijay | A61M 25/104 |
| | | | 604/103.1 |
| 6,217,547 B1 * | 4/2001 | Lee | A61L 29/049 |
| | | | 604/103 |

(Continued)

FOREIGN PATENT DOCUMENTS

| | | |
|---|---|---|
| JP | S63-288169 A | 11/1988 |
| JP | 2009-537211 A | 10/2009 |

(Continued)

OTHER PUBLICATIONS

International Search Report dated Jun. 2, 2020 received in PCT/JP2020/008008.

*Primary Examiner* — Emily L Schmidt
(74) *Attorney, Agent, or Firm* — Scully, Scott, Murphy & Presser, P.C.

(57)     ABSTRACT

A medical catheter includes a multi-lumen tube including a first lumen and a second lumen; an extension tube fixed to an end surface in a longitudinal direction of the multi-lumen tube, extending from the end surface along the longitudinal direction, and including a third lumen communicating with the first lumen; and an outer wall portion extending from the multi-lumen tube along the extension tube and configured to cover a part of an outer surface of the extension tube, the outer wall portion including a pipeline formed to communicate with the second lumen and having a part of the outer surface in an inner surface of the pipeline.

14 Claims, 20 Drawing Sheets

(56)                        References Cited

U.S. PATENT DOCUMENTS 6,706,010  B1      3/2004  Miki et al.
2007/0276325  A1    11/2007  Dzakula et al.

FOREIGN PATENT DOCUMENTS

JP          2016-135216  A      7/2016
WO          1996/020751  A1      7/1996
WO          1999/017831  A1      4/1999
WO          2007/132464  A1    11/2007

* cited by examiner

MEDICAL BALLOON CATHETER AND MANUFACTURING METHOD OF MEDICAL BALLOON CATHETER

This application is a continuation application of PCT International Application No. PCT/JP2020/008008, filed Feb. 27, 2020. The content of the PCT International Application is incorporated herein by reference.

TECHNICAL FIELD

The present disclosure relates to a medical balloon catheter and a manufacturing method of a medical balloon catheter.

BACKGROUND ART

A medical balloon catheter includes a balloon and a tube attached to a proximal end of the balloon. Each part of the balloon may be classified into a distal-end tail portion, a distal-end cone portion, a cylindrical portion, a proximal-end cone portion, and a proximal-end tail portion. The tube may include an inflatable lumen for introducing fluid into the balloon to inflate the balloon and a guidewire lumen through which a guidewire is inserted to guide the balloon catheter into a predetermined site in the body. The tube including a plurality of lumens in this manner is referred to as a multi-lumen tube.

The distal end of the multi-lumen tube includes an opening for ejecting the fluid introduced through the inflation lumen into the balloon and an opening for the guidewire lumen (GW opening). The multi-lumen tube is fixed to the balloon such that the distal end thereof is located on the proximal side of an internal space of the balloon.

On the other hand, the guide wire is introduced into the guide wire lumen through the opening (introduction opening) at the distal end of the balloon. Therefore, an extension tube passing through the internal space of the balloon for communicating the introduction opening of the distal end of the balloon and the GW opening on the proximal-end side of the internal space of the balloon is required. The extension tube is connected in series with the distal end of the multi-lumen tube. The extension tube is also referred to as an inner tube because of being accommodated inside the balloon.

U.S. Pat. No. 4,782,834 discloses a balloon catheter in which a multi-lumen tube and an extension tube are heat-sealed and joined in a state in which end surfaces orthogonal to the longitudinal direction thereof face each other.

United States Patent Application, Publication No. 2007/0276325 discloses a catheter shaft joined in a state in which a proximal-end portion of the extension tube is inserted into a distal-end opening of the guide wire lumen in the multi-lumen tube.

SUMMARY

According to an aspect of the present disclosure, a medical catheter includes a multi-lumen tube including a first lumen and a second lumen; an extension tube fixed to an end surface in a longitudinal direction of the multi-lumen tube, extending from the end surface along the longitudinal direction, and including a third lumen communicating with the first lumen; and an outer wall portion extending from the multi-lumen tube along the extension tube and configured to cover a part of an outer surface of the extension tube, the outer wall portion including a pipeline formed to communicate with the second lumen and having a part of the outer surface in an inner surface of the pipeline.

According to another aspect of the present disclosure, a manufacturing method of a medical balloon catheter includes an outer wall portion formation step of, in a multi-lumen tube including a first lumen and a second lumen, forming an end surface on which the first lumen opens and forming an outer wall portion extending along a longitudinal direction of the multi-lumen tube from part of a side wall portion of the multi-lumen tube surrounding the second lumen to a distal end side with respect to the end surface; an extension tube fixation step of making an end portion of an extension tube including a third lumen to face the end surface, disposing the extension tube at a position where the third lumen communicates with the first lumen and a side surface of the end portion is adjacent to the outer wall portion, and fixing the end portion to each of the end surface and an end edge in a circumferential direction of the outer wall portion to form a pipeline communicating with the second lumen and having part of an outer surface of the extension tube in an inner surface thereof; and a balloon fixation step of inserting the extension tube through an internal space of the balloon such that the internal space communicates with the second lumen via the pipeline and fixing the balloon to an outer circumferential portion of at least one of the multi-lumen tube, the extension tube, and the outer wall portion.

DESCRIPTION OF EMBODIMENTS

Hereinafter, a medical balloon catheter according to an embodiment of the present invention will be described. In the medical balloon catheter according to the present disclosure and the configurational members thereof, a direction along an axis is referred to as an axial direction, a direction around the axis is referred to as a circumferential direction, and a direction along a line intersecting the axis in a plane orthogonal to the axis is referred to as a diameter direction. A cross section along the axis is referred to as an axial cross section. A cross section orthogonal to the axis is referred to as an axis orthogonal cross section.

Figure 1:
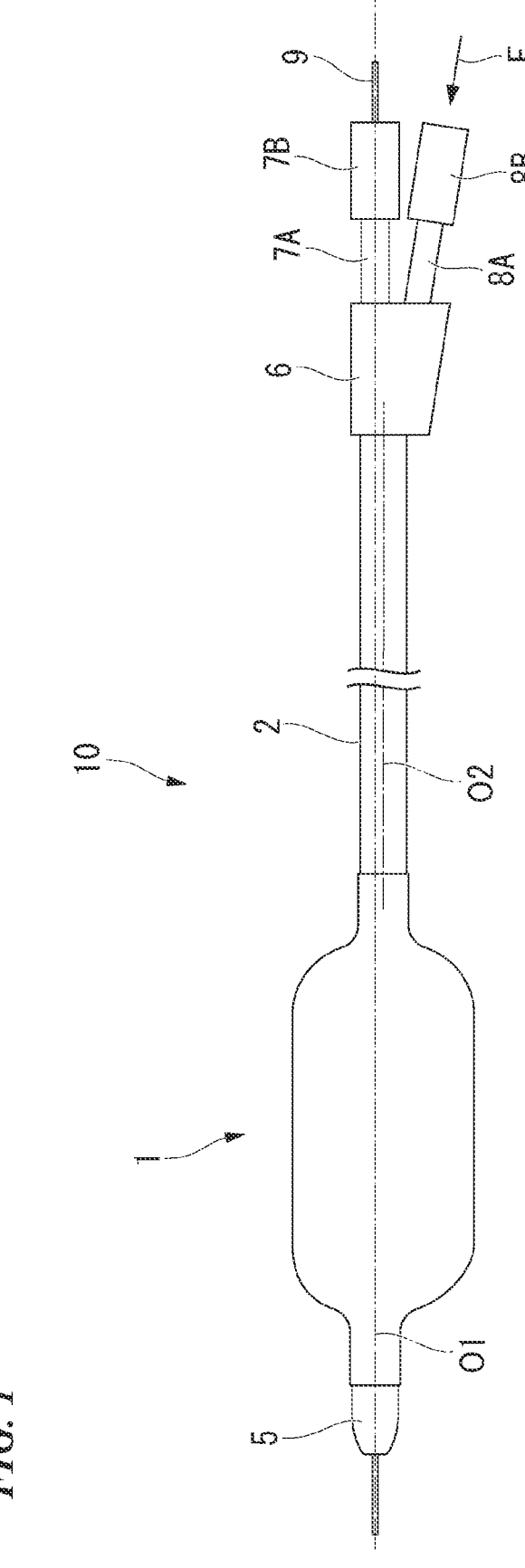
FIG. 1 is a schematic front view showing an example of a medial balloon catheter according to an embodiment of the present disclosure.

FIG. 1 is a schematic front view showing an example of a medical balloon catheter according to an embodiment of the present disclosure. As shown in FIG. 1, a balloon catheter 10 (medical balloon catheter) according to the present embodiment is an elongated member extending from a proximal end on the right side of the figure toward a distal end on the left side of the figure. The balloon catheter 10 is inserted into the luminal cavity of a patient from the distal end through a treatment tool channel of an endoscope (not shown) that is inserted into the luminal cavity of the patient.

The luminal cavity into which the balloon catheter 10 is inserted includes the gastrointestinal tract such as the esophagus, pylorus, bile duct, large intestine and the like; however, the luminal cavity is not limited to these gastrointestinal tract.

The guidewire 9 is insertable into the balloon catheter 10 such that the balloon catheter 10 can be inserted into the luminal cavity of the patient along the guidewire 9 that is indwelled in the body of the patient.

Figure 2:
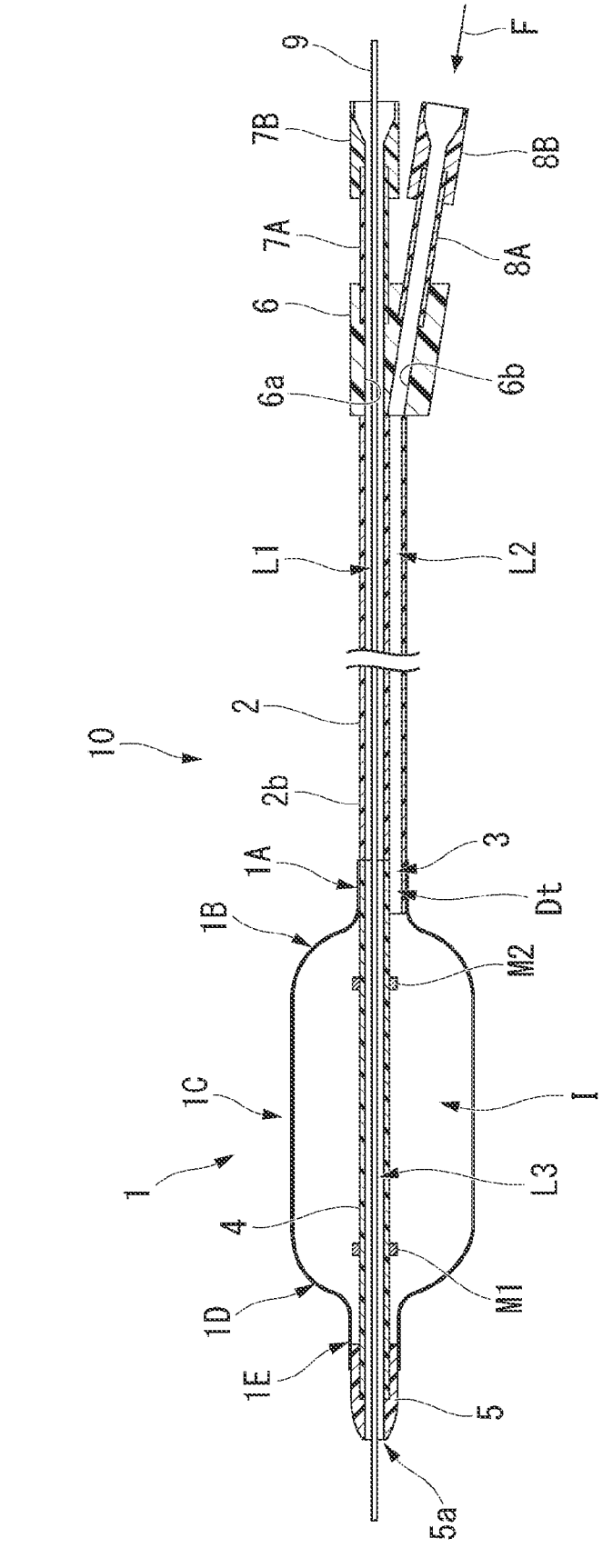
FIG. 2 is a schematic cross-sectional view showing the example of the medial balloon catheter according to the embodiment of the present disclosure.

FIG. 2 is a schematic cross-sectional view of the balloon catheter 10. The balloon catheter 10 has a distal-end convex portion 5, a balloon 1, a multi-lumen tube 2, a branch portion 6, a guidewire tube 7A, a hub 7B (on the guidewire tube side), a fluid feeding tube 8A, and a hub 8B (on the fluid feeding tube side) are provided in this sequence from the distal end toward the proximal end. The shape of the balloon 1 may be configured to have an inflated state that is inflated by introducing a fluid into the balloon 1 from the hub 8B, and a deflated state in which no fluid is introduced. FIG. 1 and FIG. 2 show the shape of the balloon 1 in the inflated state.

As shown in FIG. 2, an extension tube 4 described later, which has a guidewire lumen L3 inside, is accommodated inside the balloon 1. The multi-lumen tube 2 includes a guidewire lumen L1 and an inflation lumen L2.

The guidewire 9 is inserted into the balloon catheter 10 through a through hole 5a of the distal-end convex portion 5. A distal end of the guidewire 9 is protruded from a proximal end of the hub 7B as passing through the guidewire lumen L3 of the extension tube 4, the guidewire lumen L1 of the multi-lumen tube 2, the guidewire lumen 6a of the branch portion 6, the lumen of the guidewire tube 7A, and the through hole of the hub 7B in this sequence.

The fluid F introduced into the balloon 1 enters the inside of the balloon catheter 10 through the through hole of the hub 8B and passes through the lumen of the fluid feeding tube 8A, the fluid feeding lumen 6b of the branch portion 6, and the inflation lumen L2 of the multi-lumen tube 2 so as to be introduced into an internal space I of the balloon 1 from the proximal-end side of the balloon 1.

Each configurational element will be described in details below.

A distal-end portion of the distal-end convex portion 5 is gradually reduced in diameter and rounded toward the distal-end side. An outer diameter of the distal-end convex portion 5 excluding the distal-end portion is substantially equal to the outer diameter of the multi-lumen tube 2.

A recess portion to which the distal-end portion of the extension tube 4 is connected is formed at the proximal-end portion of the distal-end convex portion 5.

The balloon 1 is made of a resin film. The shape of the balloon 1 is a cylinder centered on the central axis O1 in the inflated state. An internal space I is formed inside the balloon 1 in the inflated state. Although it is not shown in the figures, the balloon 1 before being inserted into the treatment tool channel of the endoscope is in the deflated state, and the balloon 1 is folded into a plurality of thin blades to be wound around the outer circumference of the extension tube 4.

The outer diameter of the folded balloon catheter 10 when the balloon 1 is deflated is sized so as to pass through the luminal cavity and the treatment tool channel of the endoscope as the insertion target.

The balloon 1 includes a first tail portion 1A (proximal end tail portion), a first cone portion 1B (proximal end cone portion), a body portion 1C (cylindrical portion), a second cone portion 1D (distal end cone portion), and a second tail portion 1E (distal end tail portion) from the proximal-end side toward the distal-end side.

Figure 3:
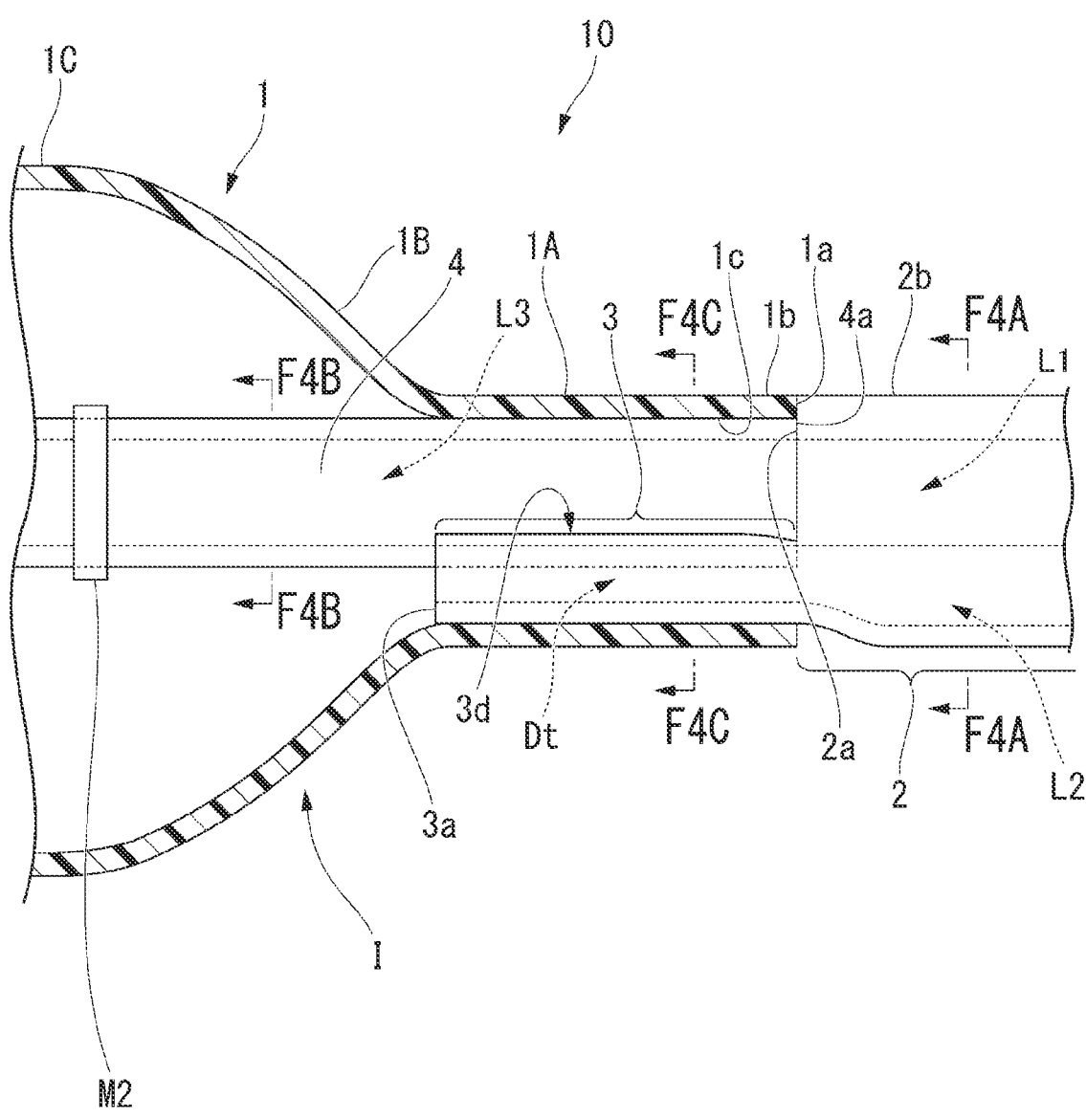
FIG. 3 is a schematic partial cross-sectional view showing a main portion of the medial balloon catheter according to the embodiment of the present disclosure.

FIG. 3 is a schematic cross-sectional view showing a main part of the balloon catheter 10 according to the present embodiment. In order to clarify the positional relationship of each member configuring the main part, FIG. 3 shows a state before joining each member by fusion. The following description also describes the state before the fusion. The shape after the fusion will be described later together with the manufacturing method.

The first tail portion 1A is formed in a cylindrical shape. As shown in FIG. 3, in the present embodiment, the outer diameter of the first tail portion 1A is substantially equal to the outer diameter of the multi-lumen tube 2.

The first tail portion 1A is fixed to at least one of the extension tube 4, the outer wall portion 3, and the multi-lumen tube 2 so as not to form a gap communicating in the axial direction.

In the present embodiment, the fusion is adopted as a method of fixing the extension tube 4 and the outer wall portion 3 to the first tail portion 1A; however, the fixing method is not particularly limited as long as the fluid F can be sealed inside.

The first cone portion 1B is a hollow portion whose diameter is gradually increased from the distal end of the first tail portion 1A toward the body portion 1C. For example, the shape of the first cone portion 1B may be a conical surface or a shape curved outward or inward from the conical surface due to a change in the change rate of the diameter. For example, the shape of the first cone portion 1B may be a bowl type, a cannonball type, a bell type, a funnel type, a horn type, or the like.

The body portion 1C is a substantially cylindrical portion having a constant outer diameter and centered on the central axis O1 that is connected to the distal-end side of the first cone portion 1B.

As shown in FIG. 2, the second cone portion 1D is a hollow portion whose diameter is gradually reduced from the distal end of the body portion 1C toward the second tail portion 1E described later. The second cone portion 1D may have the same shape as that of the first cone portion 1B.

The second tail portion 1E extends from the distal end of the second cone portion 1D toward the distal end. The second tail portion 1E is formed in the same cylindrical shape as that of the first tail portion 1A.

The inner circumferential surface of the distal-end portion of the second tail portion 1E is fixed to the outer circumferential surface of the distal-end convex portion 5 without any gap therebetween.

The balloon 1 can be inflated and deflated by the pressure of the fluid F. The balloon 1 is made of the resin material having the high compressive strength. The fluid F may be a liquid or a gas.

The material of the balloon 1 preferably has sufficient translucency. The light transmittance of the material of the balloon 1 is more preferably close to 100%. If the light transmittance of the balloon 1 is high, the subject on the other side of the balloon 1 can be observed by the observation with the objective lens of the endoscope.

The material of the balloon 1 includes the polyamide elastomer, the polyamide resin, the nylon, and the urethane; however, the material of the balloon 1 is not limited thereto.

The multi-lumen tube 2 is an elongated member including a guidewire lumen L1 (first lumen) through which the guidewire 9 is inserted and an inflation lumen L2 (second lumen) through which the fluid that inflates the balloon 1 passes. However, the multi-lumen tube 2 may have other lumens.

The outer circumferential surface 2b (outer circumferential portion) of the multi-lumen tube 2 does not have to be a cylindrical surface, and may have an elliptical or irregular cross section, for example. In the following description, an example of the cylindrical surface will be described.

The guidewire lumen L1 and the inflation lumen L2 are lumens independent from each other, and each penetrate the multi-lumen tube 2 in the longitudinal direction (axial direction) thereof.

The shape of the cross section of the guidewire lumen L1 orthogonal to the length direction is not limited to a circular shape; however, the shape will be described below with an example of a circular shape. The inner diameter of the guidewire lumen L1 is a size that allows the guidewire 9 to smoothly advance and retreat.

The shape of the cross section orthogonal to the length direction of the inflation lumen L2 is not particularly limited as long as there is no hindrance in the flowability of the fluid F and the pressure resistance performance. According to the present embodiment, a substantially semicircular shape is adopted, and the strings are arranged to be at the inner side.

Examples of the material of the multi-lumen tube 2 include the polyamide and the polyether block amide copolymer; however, the material of the multi-lumen tube 2 is not limited thereto.

As shown in FIG. 3, an end surface 2*a* is formed at the distal end of the multi-lumen tube 2. A guidewire lumen L1 is open on the end surface 2*a*. In the present embodiment, the end surface 2*a* is a plane orthogonal to the axial direction of the multi-lumen tube 2; however, the end surface 2*a* is not limited to this configuration and may be a non-plane surface such as a convex-concave surface or an uneven surface, or an inclination surface.

Figure 4A:
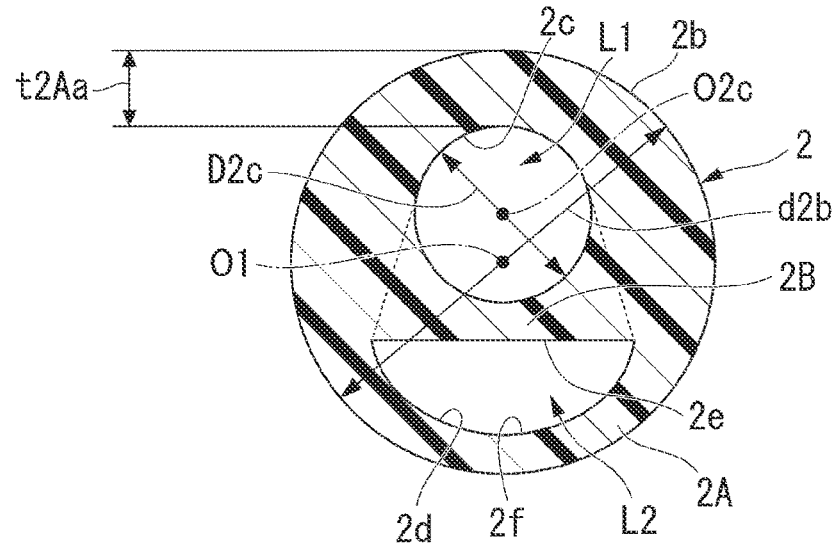
FIG. 4A is a cross-sectional view taken along an F4A-F4A line in FIG. 3.
Figure 4B:
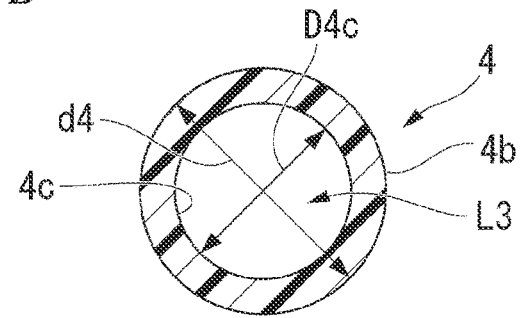
FIG. 4B is a cross-sectional view taken along an F4B-F4B line in FIG. 3.
Figure 4C:
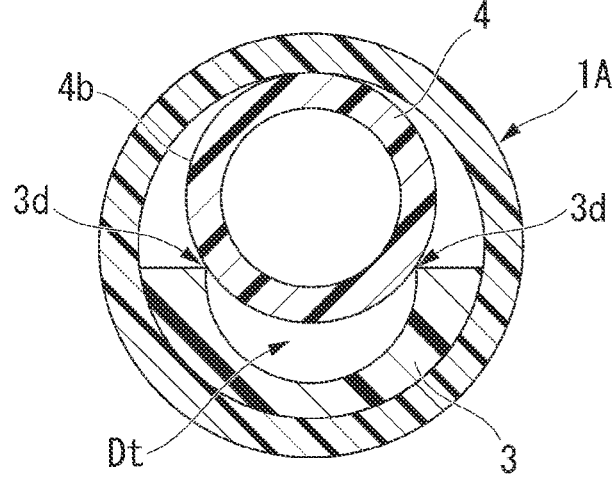
FIG. 4C is a cross-sectional view taken along an F4C-F4C line in FIG. 3.
Figure 5A:
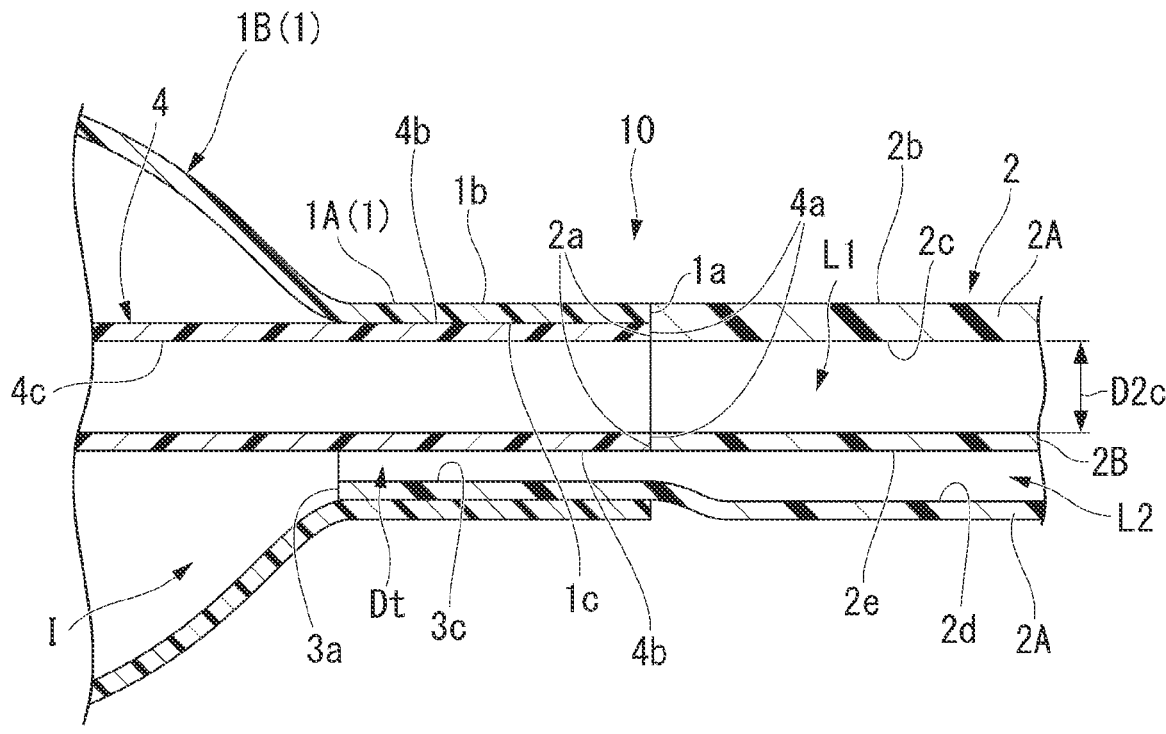
FIG. 5A is a schematic partial cross-sectional view showing an example (first example) of a cross sectional along an axial direction of the main portion of the medial balloon catheter according to the embodiment of the present disclosure.
Figure 5B:
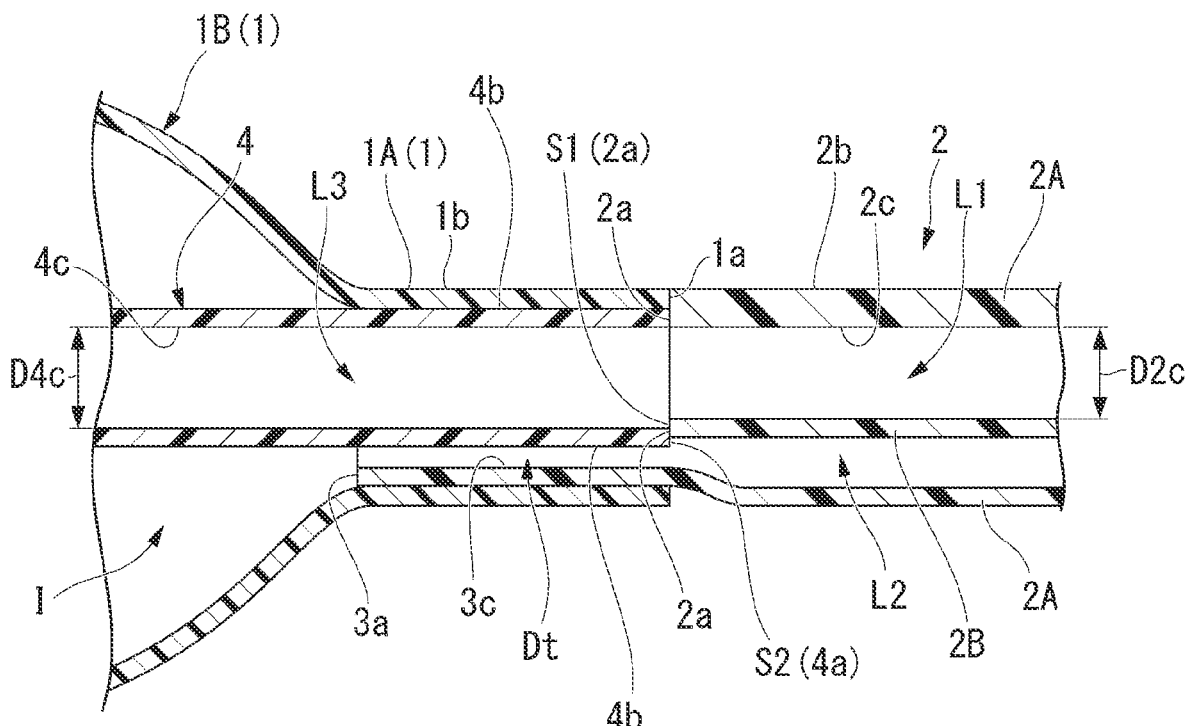
FIG. 5B is a schematically partial cross-sectional view showing an example (second example) of a cross sectional along an axial direction of the main portion of the medial balloon catheter according to the embodiment of the present disclosure.

FIG. 4A is a cross-sectional view taken along the line F4A-F4A in FIG. 3. FIG. 4B is a cross-sectional view taken along the line F4B-F4B in FIG. 3. FIG. 4C is a cross-sectional view taken along the line F4C-F4C in FIG. 3. FIG. 5A and FIG. 5B are schematic partial cross-sectional views showing examples (first example, second example) of an axial cross section of a main part of a medical balloon catheter according to the embodiment of the present disclosure.

As shown in FIG. 4A showing a cross section orthogonal to the axis, the outer diameter of the multi-lumen tube 2 (diameter of the outer circumferential surface 2*b*) is d2*b*.

The guidewire lumen L1 is formed inside a cylindrical inner circumferential surface 2*c* having an inner diameter of D2*c* (however, D2*c*<d2*b*). The central axis O2*c* of the guidewire lumen L1 is eccentric to the outer circumferential side of the central axis O1.

The inflation lumen L2 is adjacent to the guidewire lumen L1 in a direction opposite to the eccentric direction of the guidewire lumen L1 (direction from the central axis O1 toward the central axis O2*c*).

In the example shown in FIG. 4A, the inflation lumen L2 has a D-shape (approximately semi-circular shape) surrounded by a concave surface portion 2*d* curved along the outer circumferential surface 2*b* and a flat surface portion 2*e* connecting both end portions of the concave surface portion 2*d* in the circumferential direction.

The curvature radius of the concave surface portion 2*d* of the inflation lumen L2 is not particularly limited. In the example shown in FIG. 4A, the curvature radius of the concave surface portion 2*d* is smaller than the curvature radius of the outer circumferential surface 2*b* of the multi-lumen tube 2. Therefore, the thickness of the wall body between the concave surface portion 2*d* and the outer circumferential surface 2*b* is minimized at the bottom portion 2*f*.

According to such a configuration, the multi-lumen tube 2 can be divided into a side wall portion 2A and a partition wall portion 2B.

The side wall portion 2A has a tubular shape that surrounds both the guidewire lumen L1 and the inflation lumen L2 from the outside in the radial direction along the outer circumferential surface 2*b*.

The partition wall portion 2B is a wall body portion sandwiched between the guidewire lumen L1 and the inflation lumen L2. The partition wall portion 2B partitions the inside of the side wall portion 2A into the guidewire lumen L1 and the inflation lumen L2.

At least the guidewire lumen L1 opens over the entire circumference on the end surface 2*a* of the multi-lumen tube 2. In the axial cross section, at least the entire partition wall portion 2B and the side wall portion 2A surrounding the inner circumferential surface 2*c* and the partition wall portion 2B are exposed (see FIG. 5A and FIG. 5B).

As shown in FIG. 3, the extension tube 4 is fixed to the end surface 2*a* of the multi-lumen tube 2 and extends from the end surface 2*a* in the longitudinal direction of the multi-lumen tube 2.

The extension tube 4 is a tubular member having a guidewire lumen L3 into which the guidewire 9 is inserted. The proximal-end portion of the extension tube 4 is fixed to the end surface 2*a* of the multi-lumen tube 2 at the proximal-end surface 4*a* thereof. As shown in FIG. 2, the main body portion of the extension tube 4 is accommodated inside the balloon 1, and the distal-end portion of the extension tube 4 is connected to the distal-end convex portion 5 that is fixed inside the second tail portion 1E. The guidewire lumen L3 of the extension tube 4 communicates with the through hole 5*a* of the distal-end convex portion 5 on the distal-end side so as to communicate with the outside of the balloon 1 through the through hole 5*a*. Further, the guidewire lumen L3 communicates with the guidewire lumen L1 of the multi-lumen tube 2 on the proximal end side thereof; however, the guidewire lumen L3 does not communicate with the inflation lumen L2.

Since the extension tube 4 is located inside the internal space I of the balloon 1 so as to be also referred to as an inner tube.

The extension tube 4 also functions to support the balloon 1 attached to the front of the multi-lumen tube 2 so as to prevent the balloon 1 from being crushed in the axial direction.

The material of the extension tube 4 includes the polyamide and the polyether block amide copolymer; however, the material of the extension tube 4 is not limited thereto and may be any material that can be fixed to the multi-lumen tube 2. It is more preferable that the material of the extension tube 4 is a material that can be fused with the multi-lumen tube 2.

It is more preferable that the material of the extension tube 4 is the same material as the material of the multi-lumen tube 2 or a material highly compatible with the material of the multi-lumen tube 2 from the viewpoint of increasing the bonding strength with the multi-lumen tube 2.

For example, as the material of the extension tube 4 and the material of the multi-lumen tube 2 having high bonding strength and excellent flexibility, combinations of the polyamides, the polyether block amide copolymers, the polyether block amide copolymers and polyamides and the like can be mentioned.

The shape of the proximal-end surface 4*a* of the extension tube 4 can be an appropriate surface shape corresponding to the shape of the end surface 2*a* as long as it is fixed to the end surface 2*a* of the multi-lumen tube 2 without forming a gap therebetween. In the example shown in FIG. 3, the proximal-end surface 4*a* has a planar shape in close contact with the end surface 2*a*.

The position and the shape of the boundary between the proximal-end surface 4*a* and the end surface 2*a* at the joint portion after the fusion is specified according to the material of the extension tube 4 and the multi-lumen tube 2, the fixing method, and the like. For example, when the materials of the extension tube 4 and the multi-lumen tube 2 are different from each other, they can be specified by the difference in the material components. That is, it is possible to specify the corresponding position of the boundary surface due to the change of the material component. In addition, it is possible to specify the position of the boundary surface by the change in the transmittance of the material and in a case of using an adhesive, it is possible to specify the position of the adhesive layer.

FIG. 4B shows a cross section orthogonal to the axis of the extension tube 4; however, according to the present embodiment, the extension tube 4 has a cylindrical shape. In the example shown in FIG. 4B, the outer circumferential surface 4b (outer surface, outer circumferential portion) and the inner circumferential surface 4c are both cylindrical and coaxial with each other. However, the outer circumferential surface 4b and the inner circumferential surface 4c may not be cylindrical or may be non-coaxial with each other.

The guidewire lumen L3 of the extension tube 4 is formed so as to be surrounded by the inner circumferential surface 4c, and the guidewire lumen L3 has a diameter D4c through which the guidewire 9 is insertable. The diameter D4c may be equal to or different from the inner diameter D2c of the inner circumferential surface 2c surrounding the guidewire lumen L1 of the multi-lumen tube 2.

The size d4 of the outer diameter of the extension tube 4 is preferably a size that fits in a region of the end surface 2a of the multi-lumen tube 2.

However, if the proximal-end surface 4a of the extension tube 4 can be brought into close contact with the end surface 2a of the multi-lumen tube 2 due to thermal deformation at the time of joining with the multi-lumen tube 2 as described later, the size d4 may be the value such that the proximal-end surface 4a extends from the partition wall portion 2B and beyond the flat surface portion 2e to partially protrude into the inflation lumen L2.

The outer diameter d4 of the extension tube 4 may be equal to or larger than 0.4 times and equal to or smaller than 0.7 times of the outer diameter d2b of the multi-lumen tube 2.

When the value of the outer diameter d4 of the extension tube 4 is within this range, it is easy to secure a space for circulating the fluid F supplied from the inflation lumen L2 to the outside of the extension tube 4. Further, even if the guidewire lumen L3 having the diameter suitable for the guidewire 9 to advance and retract is secured inside the extension tube 4, the thickness of the extension tube 4 does not become too thin. Therefore, it is possible to prevent the extension tube 4 from being bent and the cross-sectional shape of the guidewire lumen L3 being distorted and narrowed to deteriorate the insertability of the guide wire.

It is preferable that the guidewire lumen L1 of the multi-lumen tube 2 and the guidewire lumen L3 of the extension tube 4 have the same inner diameter, and the guidewire lumen L1 and the guidewire lumen L3 communicate with each other without a step (see first example shown in FIG. 5A). The configuration can be realized by joining the guidewire lumen L1 and the guidewire lumen L3 with each other in a state in which the guidewire lumen L1 of the multi-lumen tube 2 and the guidewire lumen L3 of the extension tube 4 have the same inner diameter and one core metal is inserted through both the guidewire lumen L1 and the guidewire lumen L3. In this way, since there is no step at the boundary between the guidewire lumen L1 and the guidewire lumen L3, the guide wire can be smoothly inserted.

However, it is possible to improve the insertability of the guidewire 9 to be inserted by making the guidewire lumen L3 of the extension tube 4 to be larger in diameter than the guidewire lumen L1 of the multi-lumen tube 2 (see second example shown in FIG. 5B).

In the example shown in FIG. 2, a marker M1 and a marker M2 provided such that the surgeon can detect an effective range of the balloon 1 are provided on the outer circumferential portion of the extension tube 4. The effective range of the balloon 1 is defined as a range in which the inflation function of the luminal cavity is effective, more specifically, that is a range of the body portion 1C in the axial direction.

The marker M1 corresponds to the position of the distal end of the body portion 1C while the marker M2 corresponds to the position of the proximal end of the body portion 1C, and the marker M1 and the marker M2 are arranged on the outer circumferential portion of the extension tube 4.

The marker M1 and the marker M2 are X-ray opaque markers that can be photographed by X-rays; however, the types of markers are not particularly limited thereto. When the balloon 1 is translucent, the marker M1 and the marker M2 are preferably formed of an opaque material or a colored material such that they are observable through an imaging device of the endoscope.

For example, the materials of the marker M1 and the marker M2 include the metals such as gold, platinum, iridium, and tungsten, alloys thereof, and barium sulfate. However, the materials of the marker M1 and the marker M2 are not limited thereto.

In the example shown in FIG. 2, the shapes of the marker M1 and the marker M2 are ring-shaped fixed to the entire circumference of the outer circumferential portion of the extension tube 4; however, the shapes of the marker M1 and the marker M2 are not limited thereto.

The methods for attaching the marker M1 and marker M2 to the extension tube 4 include the adhesion and the aging; however, the methods are not limited thereto.

It is more preferable that the outer diameter of the extension tube 4 is large in that the marker M1 and the marker M2 can be easily increased in dimension. Since the marker M1 and marker M2 can be increased in dimension, the detection becomes easier.

It is more preferable that the thickness of the extension tube 4 is thicker such that it is easy to attach the marker M1 and marker M2. In this case, since the rigidity of the extension tube 4 is improved, the guidewire lumen L3 is less likely to be narrowed at the portion where the marker M1 and marker M2 are attached. As a result, the guidewire 9 can be smoothly inserted and advanced/retracted.

As shown in FIG. 4C, the outer wall portion 3 is located outside the outer circumferential surface 4b (outer surface) of the proximal-end portion of the extension tube 4.

The outer wall portion 3 is a plate-shaped protrusion having a substantially U-shaped cross section orthogonal to the length direction, and extends from the distal end of the multi-lumen tube 2 along the extension tube 4. The outer wall portion 3 is configured to cover part of the outer circumferential surface 4b at the outside of the extension tube 4 in a state in which both lateral sides 3d in the circumferential direction are joined (or close to) the outer circumferential surface of the extension tube and the portion between the lateral sides 3d is separated from the outer circumferential surface 4b of the extension tube 4. In other words, an arch of the U-shaped groove of the outer wall portion 3 is closed by the outer circumferential surface 4b of the extension tube 4, and a pipeline Dt is formed. The pipeline Dt communicates with the inflation lumen L2 of the multi-lumen tube 2. Therefore, the fluid that has passed through the inflation lumen L2 of the multi-lumen tube 2 passes through the pipeline Dt before entering the internal space I of the balloon 1.

According to the present embodiment, the outer wall portion 3 is configured to not to protrude outward from the outer circumferential surface 2b of the multi-lumen tube 2 in the radial direction. Further, since the outer wall portion 3 is inserted into the inside of the first tail portion 1A of the balloon 1, it is in a slightly bent state.

The outer wall portion 3 may be formed of, for example, a substantially U-shaped plate-shaped protrusion in which a part of the side wall portion 2A of the multi-lumen tube 2 protrudes from the end surface 2a of the multi-lumen tube 2.

As will be described later, according to the present embodiment, the outer wall portion 3 is formed by cutting off the distal end of the multi-lumen tube 2 as leaving a part of the side wall portion 2A along the inflation lumen L2. Therefore, the multi-lumen tube 2 and the outer wall portion 3 are formed to have an integral structure.

However, the outer wall portion 3 may be formed as, for example, a member separate from the multi-lumen tube 2. In this case, the outer wall portion 3 may be fixed to the distal end of the multi-lumen tube 2, for example. In this case, it is preferable to use the same or similar material as the material of the outer wall portion 3 and the material of the multi-lumen tube 2 from the viewpoint of bondability. Examples of the materials used for forming the outer wall portion 3 and the multi-lumen tube 2 include polyamides, polyether block amide copolymers, combinations of polyether block amide copolymers and polyamides, and the like.

Next, the branch portion 6 will be described.

As shown in FIG. 2, the branch portion 6 is fixed to the proximal end portion of the multi-lumen tube 2. The branch portion 6 has a guidewire lumen 6a and a fluid feeding lumen 6b.

The guidewire lumen 6a is a through hole through which the guidewire 9 can be inserted, and communicates with the guidewire lumen L1.

The fluid feeding lumen 6b is a through hole that communicates with the inflation lumen L2. The cross section orthogonal to the axis of the fluid feeding lumen 6b may be D-shaped or circular as same as in the inflation lumen L2.

A guidewire tube 7A is connected to the proximal end of the guidewire lumen 6a. The guidewire tube 7A is a tubular member through which the guidewire 9 extending from the proximal end of the guidewire lumen 6a is inserted therein. The inner diameter of the guidewire tube 7A is equal to the inner diameter of the guidewire lumen 6a.

A hub 7B for guiding the guidewire 9 to the lumen of the guidewire tube 7A is provided at the proximal end of the guidewire tube 7A.

A fluid feeding tube 8A is connected to the proximal-end portion of the fluid feeding lumen 6b. The fluid feeding tube 8A delivers and discharges the fluid F in the inflation lumen L2 through the fluid feeding lumen 6b.

A hub 8B being connectable to a fluid supply device (not shown) capable of supplying and sucking the fluid F is provided at the proximal end of the fluid feeding tube 8A.

With such a configuration, a guidewire insertion pipeline through which the guidewire 9 is insertable is formed by providing the guidewire tube 7A, the guidewire lumen 6a, the guidewire lumen L1 of the multi-lumen tube 2, the guidewire lumen L3 of the extension tube 4, and the through hole 5a in the longitudinal direction of the balloon catheter 10.

Similarly, a fluid feeding pipeline communicating from the hub 8B to the internal space I of the balloon 1 is formed in the longitudinal direction of the balloon catheter 10 by the fluid feeding tube 8A, the fluid feeding lumen 6b, the inflation lumen L2, and the pipeline Dt.

Next, an example of a manufacturing method of the balloon catheter 10 will be described.

The manufacturing method of the balloon catheter 10 includes performing an outer wall portion forming step, an extension tube fixing step, and a balloon fixing step after the balloon 1 is prepared.

The manufacturing method of the balloon 1 is not particularly limited. For example, the balloon 1 may be manufactured by blow molding using a shaping mold that transfers the shape in the inflated state.

Figure 6:
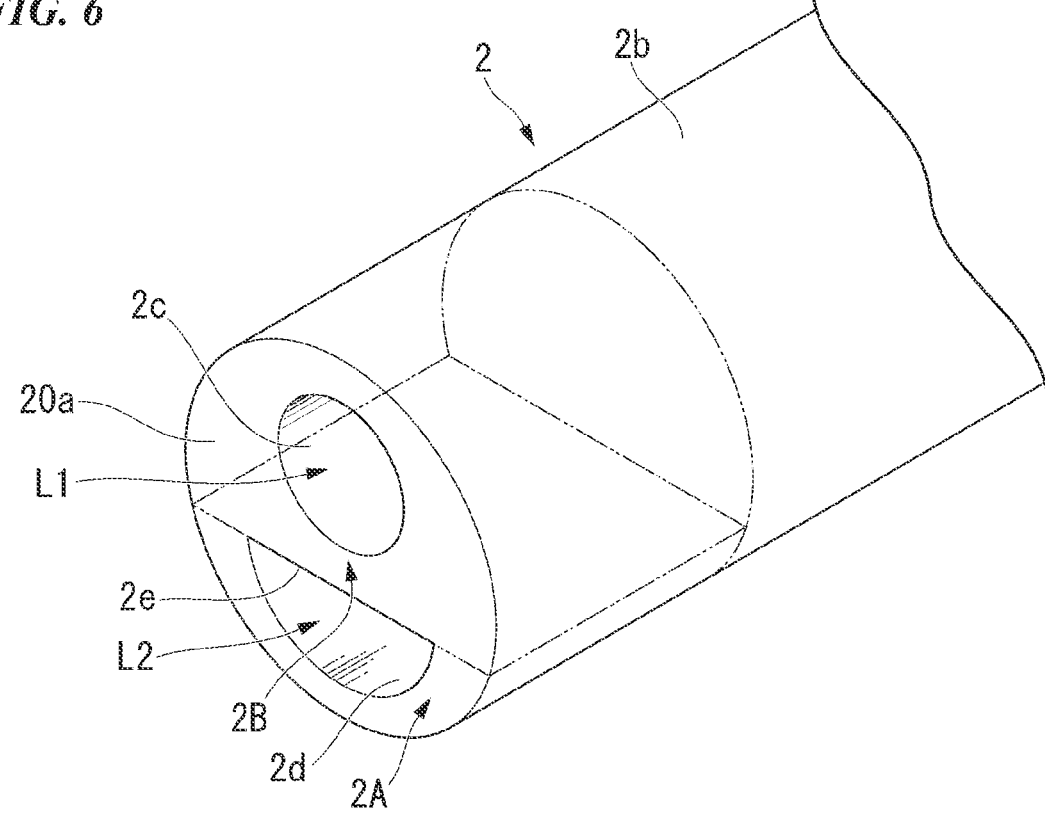
FIG. 6 is a perspective view showing an example of an outer-wall formation process in a manufacturing method of the medial balloon catheter according to the embodiment of the present disclosure.
Figure 7:
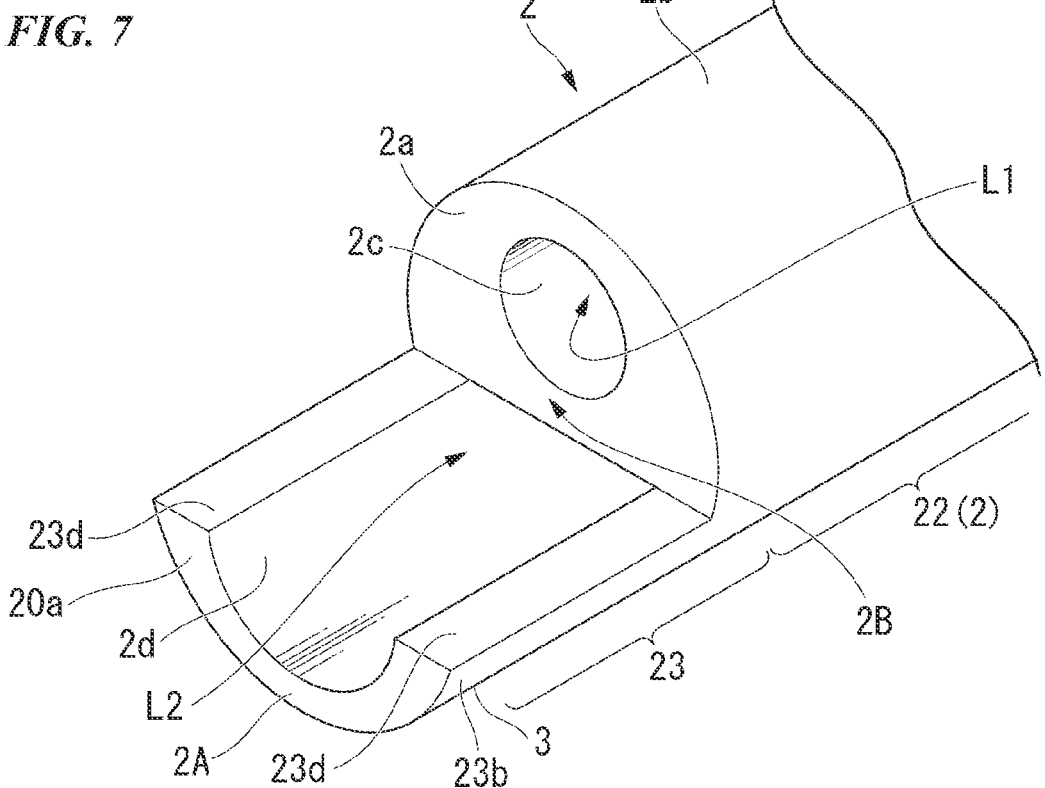
FIG. 7 is a perspective view showing the example of the outer-wall formation process.

FIG. 6 and FIG. 7 are perspective views showing an example of the outer wall portion forming step in the manufacturing method of medical balloon catheter according to the embodiment of the present disclosure.

In the outer wall portion forming step, the outer wall portion 3 is formed at the distal end of the multi-lumen tube 2. The outer wall portion 3 may be formed by being added to the multi-lumen tube 2; however, an example in which the outer wall portion 3 is formed by cutting off the distal-end portion of the multi-lumen tube 2 will be described below.

As shown in FIG. 6, the shape of the multi-lumen tube 2 (multi-lumen tube for processing) before the formation of the outer wall portion 3 is a cylindrical shape in which the guidewire lumen L1 and the inflation lumen L2 penetrate from the distal-end surface (distal end) 20a in the longitudinal direction.

After that, as shown in FIG. 7, at the distal-end portion of the multi-lumen tube 2, the guidewire lumen L1 side including the partition wall portion 2B is cut off such that a part of the side wall portion 2A is remained. A cutting depth in the radial direction is not particularly limited as long as the partition wall portion 2B is removed.

The end surface 2a is formed by the cutting surface in the radial direction. An end surface 23d (end edge) extending in the longitudinal direction is formed by the cutting surface in the axial direction.

As a result, the outer wall portion 3 formed of a substantially U-shaped plate-shaped protrusion protruding from the end surface 2a is formed. The outer wall portion 3 is formed by cutting out the side wall portion 2A forming the outer wall of the inflation lumen L2, and the concave surface portion 2d of the inflation lumen L2 is exposed between each of the end surfaces 23d.

The outer wall portion 3 is continuous with the side wall portion 2A of the multi-lumen tube 2 without having a boundary surface and a seam therebetween, and the outer wall portion 3 is made of the same material as that of the side wall portion 2A.

As described above, the outer wall portion forming step if completed.

According to the above-described outer wall portion forming step, it is easy to form the outer wall portion 3 as compared with the case in which the outer wall portion 3 is formed by joining another member to the distal end of the multi-lumen tube 2. Further, by changing the cutting length, the cutting depth, and the cutting shape, the outer wall portion 3 having various shapes can be easily formed.

After the outer wall portion forming step, the extension tube fixing step and the balloon fixing step are carried out in this sequence or in parallel.

Hereinafter, an example in which the extension tube fixing step and the balloon fixing step are carried out in parallel will be described. Therefore, the extension tube fixing step and the balloon fixing step are referred to as a fixing step. The heat fusion is used as the fixing method.

Figure 8:
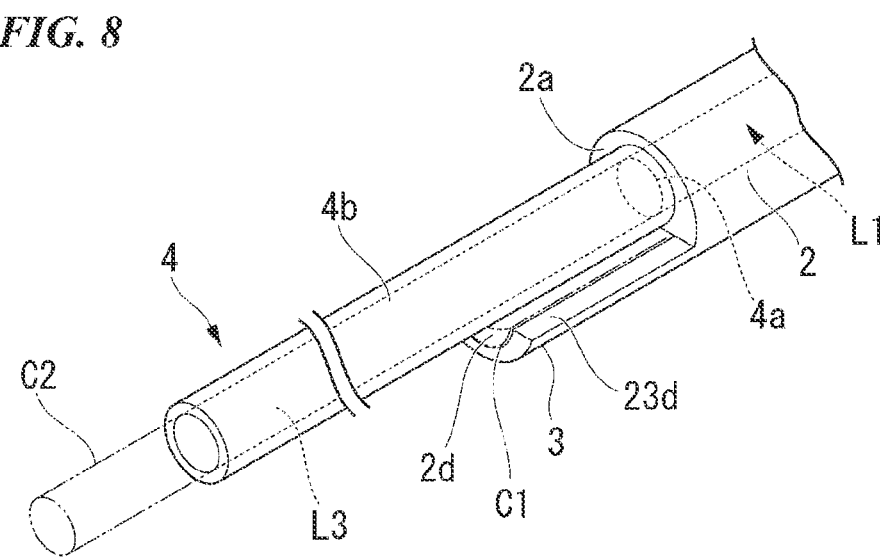
FIG. 8 is a perspective view showing an example of a fixation process in the manufacturing method of the medial balloon catheter according to the embodiment of the present disclosure.
Figure 9:
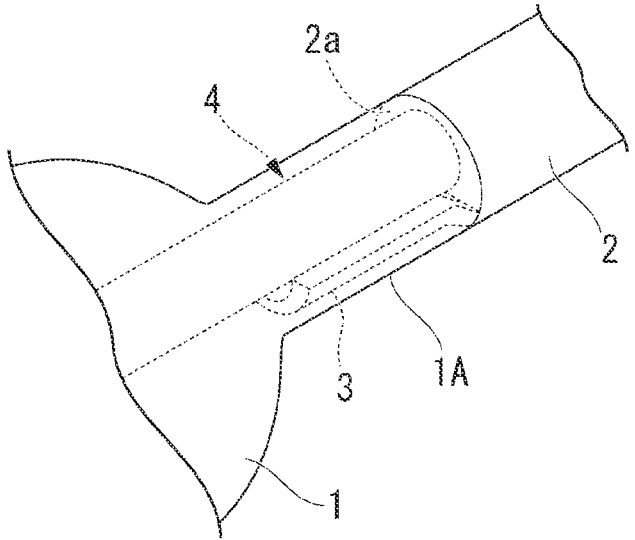
FIG. 9 is a perspective view showing the example of the fixation process.
Figure 10:
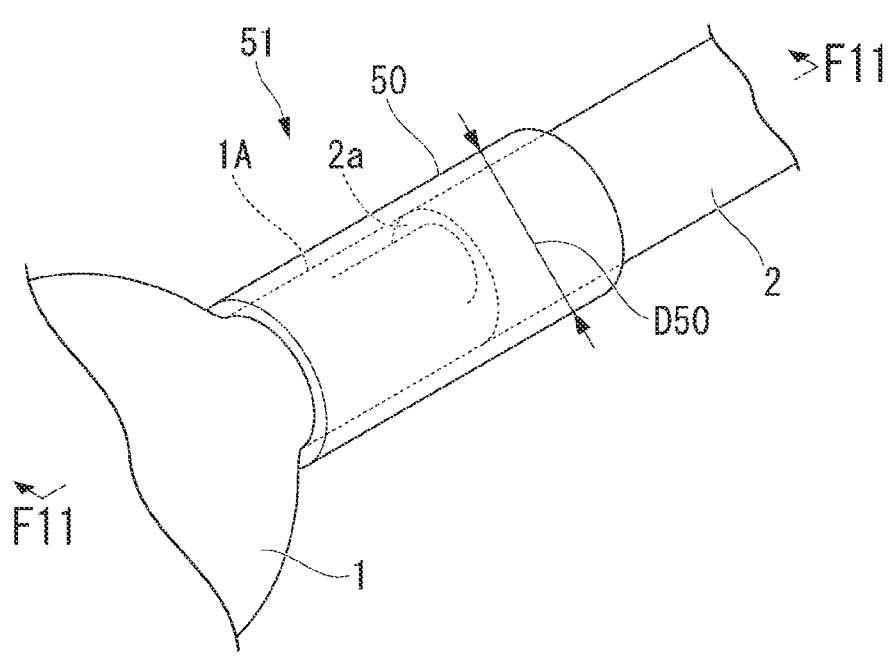
FIG. 10 is a perspective view showing the example of the fixation process.

FIG. 8 to FIG. 10 are perspective views showing an example of the fixing step in the manufacturing method of a medical balloon catheter according to an embodiment of the present disclosure.

In the fixing step, the multi-lumen tube 2, the extension tube 4, and the balloon 1 are arranged in a positional relationship to be fixed.

For example, as shown in FIG. 8, the proximal-end surface 4*a* of the extension tube 4 and the end surface 2*a* of the multi-lumen tube 2 are brought into contact with each other in a state in which the core metal C2 is inserted through the guidewire lumen L1 and the guidewire lumen L3. When the inner diameters of the guidewire lumen L1 and the guidewire lumen L3 are equal to each other, a rod-shaped metal having an outer diameter equal to the inner diameter of each of the guidewire lumen L1 and the guidewire lumen L3 is used as the core metal C2. Even if the inner diameters of the guidewire lumen L1 and the guidewire lumen L3 are different from each other, in a case in which the inner diameter of the guidewire lumen L3 in the vicinity of the joint portion is the same as that of the guidewire lumen L1, the rod-shaped metal may be used as the core metal C2.

The core metal C2 is used to form the shape of the inner circumferential surfaces of the guidewire lumen L1 and the guidewire lumens L3 at the time during the fusion, which will be described later.

For example, in a case in which a step or a tapered portion is formed at the joint portion between the end surface 2*a* and the extension tube 4, the step shape or tapered shape may be formed on the outer circumferential surface of the core metal C2.

Hereinafter, an example in which the inner diameters of the guidewire lumen L1 and the guidewire lumen L3 are the same with each other will be described.

The outer circumferential surface 4*b* of the extension tube 4 arranged along the core metal C2 may be in contact with or separated from each end surface 23*d* of the outer wall portion 3.

The outer circumferential surface 4*b* of the extension tube 4 may protrude toward the concave surface portion 2*d* from the end surface 23*d* of the outer wall portion 3.

A core metal C1 extending from the inflation lumen L2 is arranged between the concave surface portion 2*d* of the outer wall portion 3 and the extension tube 4. The core metal C1 forms a cross-sectional shape of a pipeline Dt along the extension tube 4. For example, the cross section orthogonal to the axis of the core metal C1 according to the present embodiment is crescent-shaped. However, the cross-sectional shape of the core metal C1 is not limited to this configuration, and a core metal having an arc in a part of the cross-sectional shape, such as a substantially semicircular shape, can be preferably adopted.

Thereafter, as shown in FIG. 9, the extension tube 4 and the outer wall portion 3 are inserted into the balloon 1. In the present embodiment, the outer diameter of the first tail portion 1A is substantially equal to the outer diameter of the outer circumferential surface 2*b* such that, as shown in FIG. 3, the end surface 1*a* of the first tail portion 1A is in contact with the end surface 2*a*. The outer wall portion 3 is pressed toward the extension tube 4 by being inserted to the inside of the first tail portion 1A.

Figure 11:
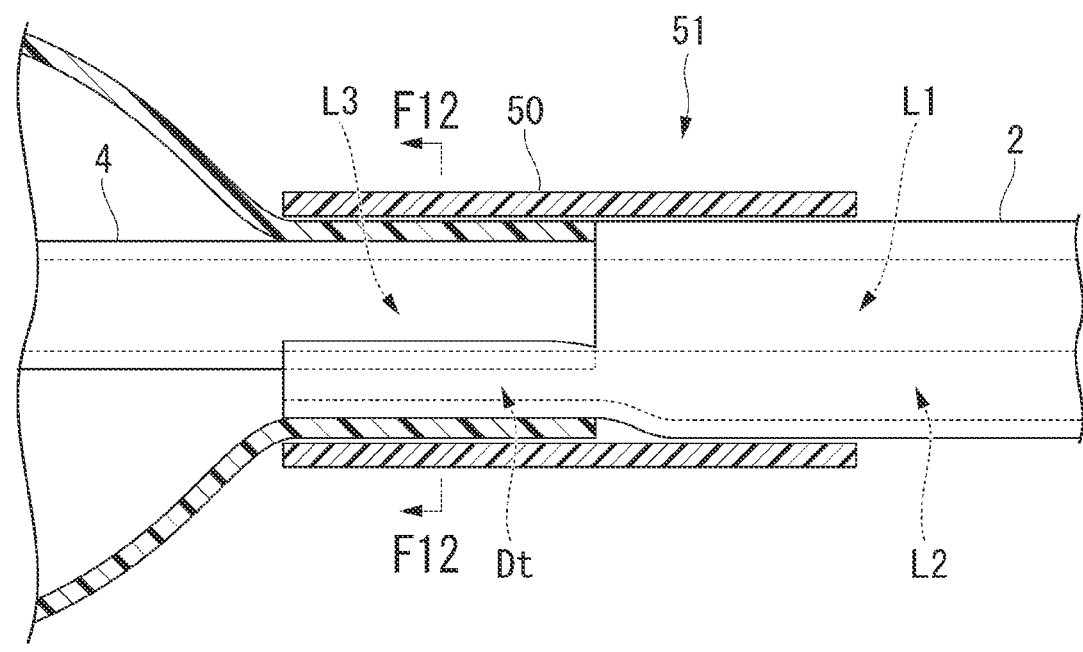
FIG. 11 is a cross-sectional view taken along an F11-F11 line in FIG. 10.

In FIG. 9, the balloon 1 is shown in the inflated state for easy viewing (the same situation is shown in FIG. 10 and FIG. 11); however, it is not necessary to make the balloon 1 to be in the inflated state. According to the present embodiment, the balloon 1 is in a non-inflated state in which a space through which the extension tube 4 and the outer wall portion 3 are insertable is formed in the central portion of the balloon 1.

Thereafter, as shown in FIG. 10, a tubular heat-shrinkable tube 50 that covers the first tail portion 1A and the multi-lumen tube 2 in the vicinity of the end surface 2*a* is attached so as to form an assembly body 51. The inner diameter of the heat-shrinkable tube 50 and an outer diameter D50 are larger than the outer diameter d2*b* of the multi-lumen tube 2.

An arrangement of each member before the fixing in the heat-shrinkable tube 50 will be described.

Figure 12:
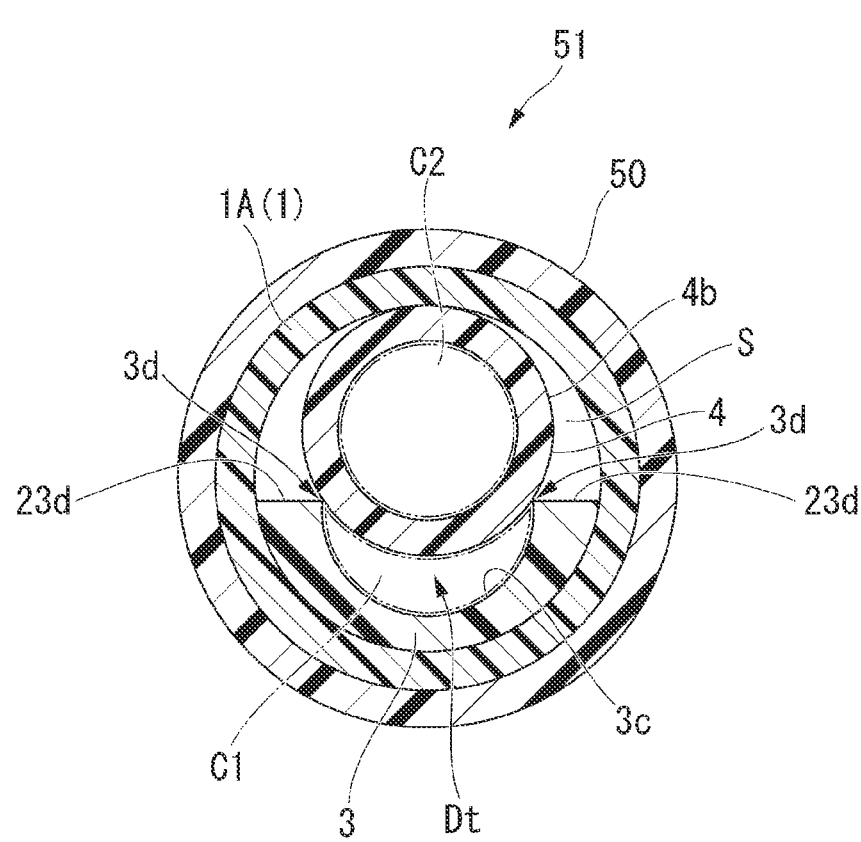
FIG. 12 is a cross-sectional view taken along an F12-F12 line in FIG. 11.

FIG. 11 is a cross-sectional view taken along the line F11-F11 in FIG. 10. FIG. 12 is a cross-sectional view taken along the line F12-F12 in FIG. 11.

As shown in FIG. 11, the outer diameter of the first tail portion 1A and the outer diameter of the multi-lumen tube 2 are substantially equal to each other. Therefore, the heat-shrinkable tube 50 can be attached to the outer circumference of the first tail portion 1A and the multi-lumen tube 2.

The outer wall portion 3 is bent when inserted inside the first tail portion 1A and is pressed against the outer circumferential surface 4*b* of the extension tube 4. As a result, as shown in FIG. 12, the lateral side 3*d* of the end surface 23*d* comes into contact with or approaches the outer circumferential surface 4*b*.

However, since the core metal C1 is arranged between the inner circumferential surface 3*c* and the outer circumferential surface 4*b*, the inner circumferential surface 3*c* excluding each lateral side 3*d* faces the extension tube 4 with the core metal C1 sandwiched therebetween.

In this state, a gap S is formed between the outer circumferential surface 4*b* of the extension tube 4 not covered by the outer wall portion 3 and the first tail portion 1A.

Thereafter, the portion of the heat-shrinkable tube 50 in the assembly body 51 is clamped by the heat-fusion device to pressurize and heat.

Figure 13:
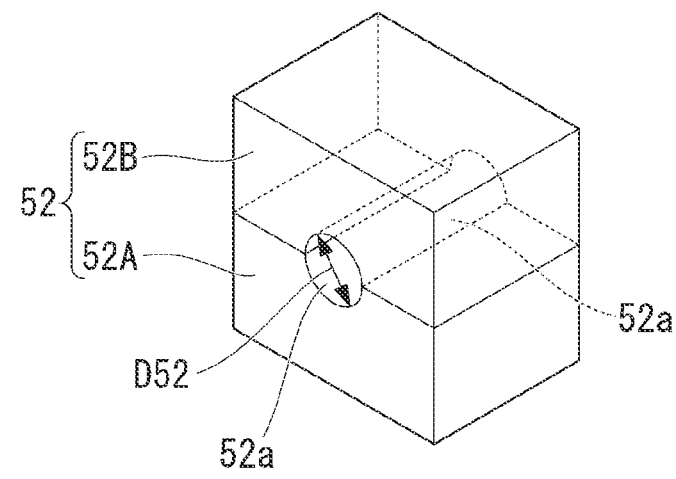
FIG. 13 is a perspective view showing an example of a fusion device used in the fixation process in the manufacturing method of the medial balloon catheter according to the embodiment of the present disclosure.
Figure 14:
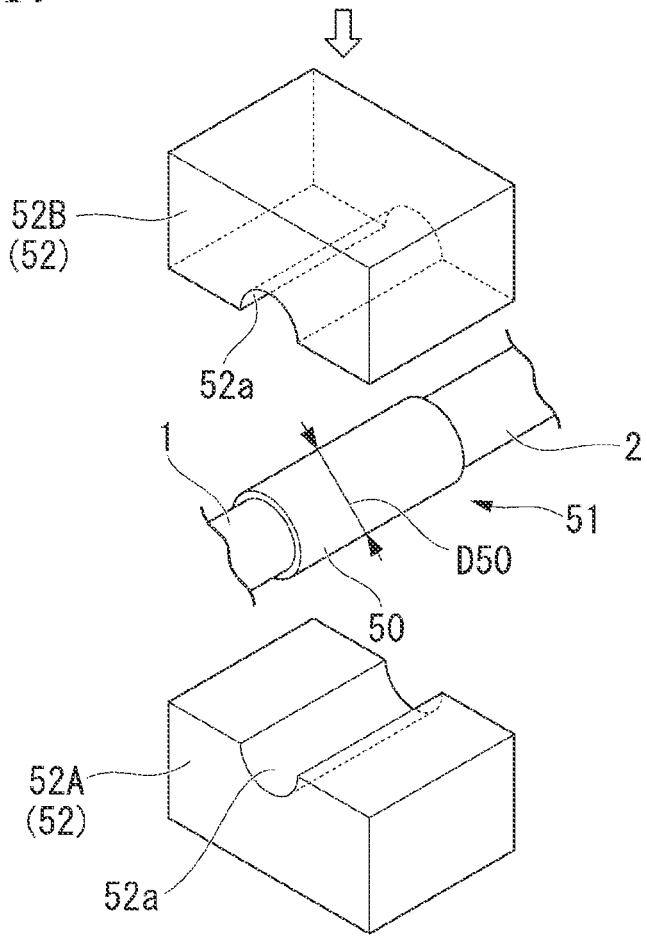
FIG. 14 is a perspective view showing an example of a heat fusion in the fixation process.
Figure 15:
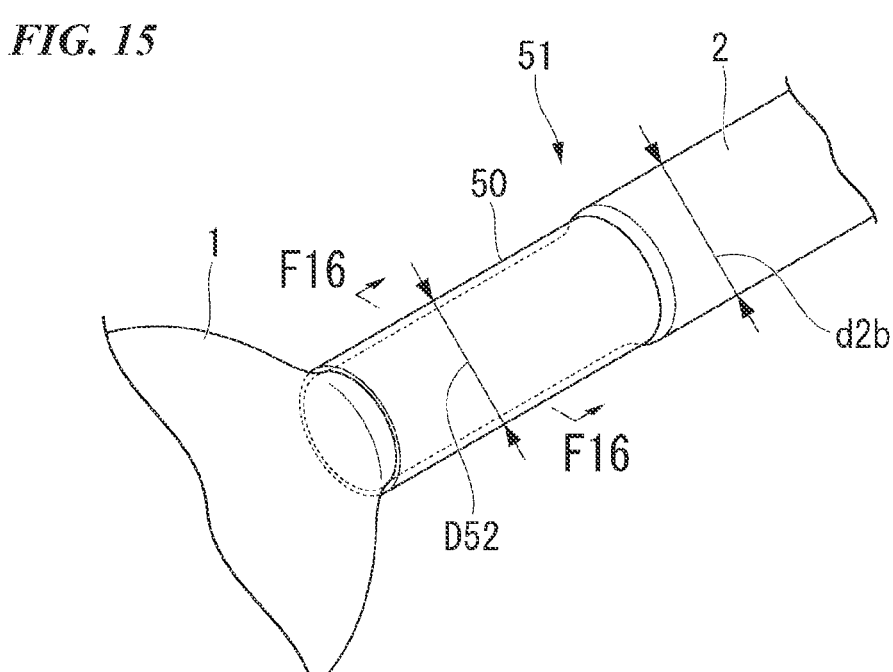
FIG. 15 is a perspective view showing an appearance of the medical balloon catheter according to the embodiment of the present disclosure.
Figure 16:
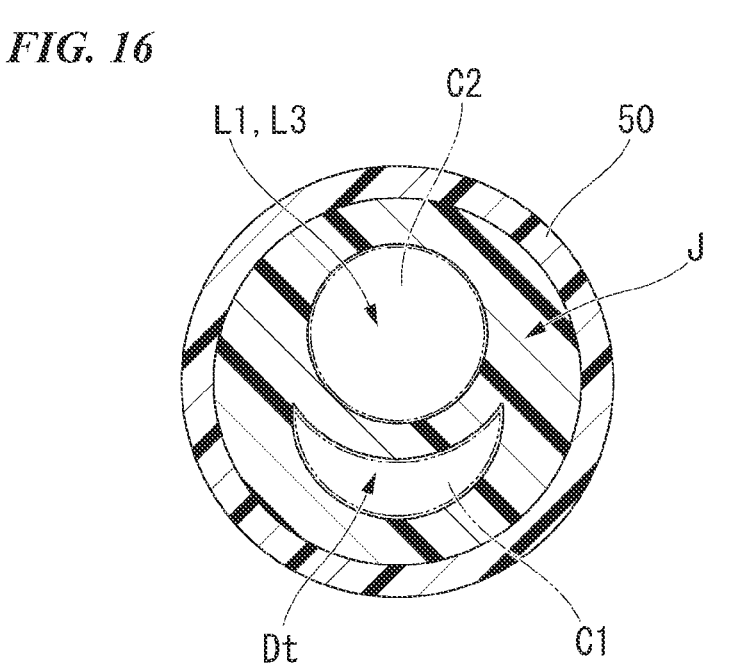
FIG. 16 is a cross-sectional view taken along an F16-F16 line in FIG. 15.

FIG. 13 is a perspective view showing an example of the fusion device used in the fixing step in the manufacturing method of a medical balloon catheter according to the embodiment of the present disclosure. FIG. 14 is a perspective view showing an example of the heat fusion in the same fixing step. FIG. 15 is a perspective view showing an appearance of the medical balloon catheter at the end of the heat fusion. FIG. 16 is a cross-sectional view taken along the line F16-F16 in FIG. 15.

As shown in FIG. 13, the fusion device 52 includes a first heating portion 52A and a second heating portion 52B. Each of the first heating portion 52A and the second heating portion 52B includes a heating surface 52*a* having a semicircular cross section. When the first heating portion 52A and the second heating portion 52B come into contact with each other, a cylindrical surface with a diameter D52 is formed by each heating surface 52*a*. The diameter D52 is equal to or less than the outer diameter d2*b* of the multi-lumen tube 2 and smaller than the outer diameter D50 of the heat-shrinkable tube 50.

As shown in FIG. 14, the heat-shrinkable tube 50 of the assembly body 51 is arranged between the heating surfaces 52*a*. Thereafter, the heat-shrinkable tube 50 is clamped between the heated heating surfaces 52*a*.

The heat-shrinkable tube 50 shrinks due to the heat from each heating surface 52*a* and is accommodated inside each closed heating surface 52*a*. The first tail portion 1A, the multi-lumen tube 2, the extension tube 4, and the outer wall portion 3 covered by the heat-shrinkable tube 50 are pressed in the radial direction and heated by the heat conduction through the heat-shrinkable tube 50.

Inside the heat-shrinkable tube 50, the first tail portion 1A, the multi-lumen tube 2, the extension tube 4, and the outer wall portion 3 are melted and heat-sealed at each abutting portion therebetween.

Thus, the fixation of the extension tube 4 and the multi-lumen tube 2 and the fixation of the extension tube 4 and the outer wall portion 3 are completed.

FIG. 15 shows the appearance of the assembly body 51 in which the fixation is completed. The heat-shrinkable tube 50 is shrinked due to the heat, and the outer diameter thereof becomes the diameter D52, which is smaller than d2*b*, such that the range of the heat-shrinkable tube 50 is reduced.

Inside the heat-shrinkable tube 50, as shown in FIG. 16, the gap S (see FIG. 12) before fusion is eliminated. Inside the heat-shrinkable tube 50, a joint body J is formed in which the resins abutting each other are heat-sealed with each other.

The shape of the core metal C2 is transferred to the guide wire lumen L1 and the guidewire lumen L3 in the heat-shrinkable tube 50. The molten outer wall portion 3 and the extension tube 4 are in close contact with each other on the outer circumferential portion of the core metal C1, and the pipeline Dt along the outer shape of the core metal C1 is formed.

Thereafter, the assembly body 51 is removed from the fusion device 52. After the joint body J has solidified, the heat-shrinkable tube 50 is removed. In this manner, the fixing process is completed.

Figure 17:
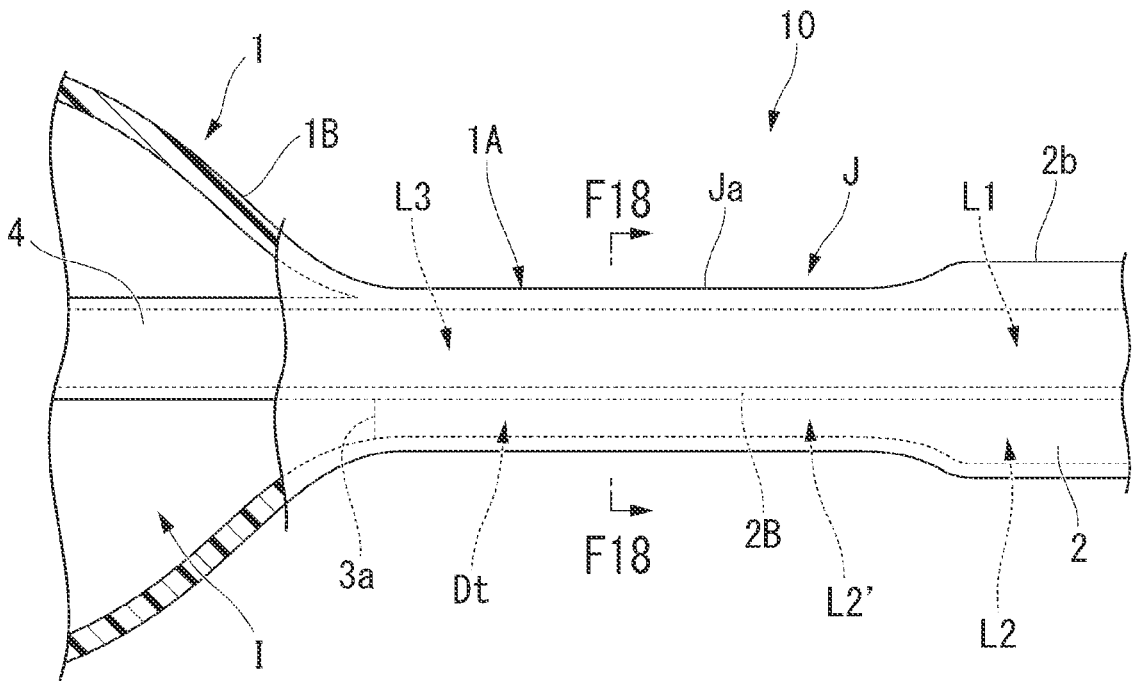
FIG. 17 is a front view showing the appearance of the medical balloon catheter according to the embodiment of the present disclosure.
Figure 18:
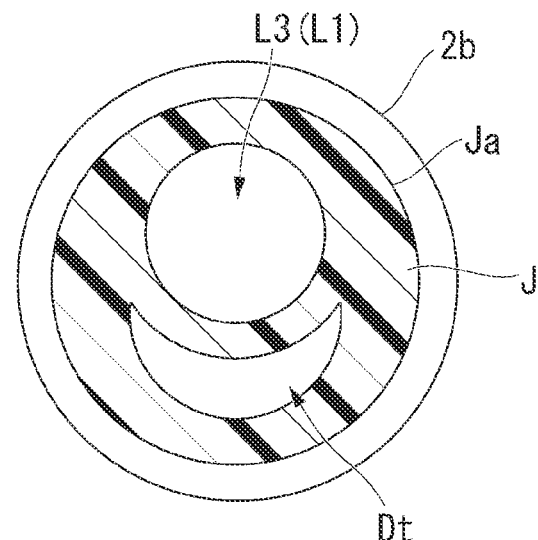
FIG. 18 is a cross-sectional view taken along an F18-F18 line in FIG. 17.

The main parts of the balloon catheter 10 after the fixation is completed are shown in FIG. 17 and FIG. 18.

FIG. 17 is a front view showing the appearance of the medical balloon catheter according to the embodiment of the present disclosure. FIG. 18 is a cross-sectional view taken along the line F18-F18 in FIG. 17.

As shown in FIG. 17, the first tail portion 1A of the balloon 1 configures a part of the outer circumferential surface Ja of the joint body J together with the outer circumferential surface 2*b* of the distal-end portion of the multi-lumen tube 2. The outer diameter of the outer circumferential surface Ja is smaller than that of the outer circumferential surface 2*b* that is not covered by the heat-shrinkable tube 50, and a constriction is formed at the distal-end portion of the multi-lumen tube 2.

The guidewire lumen L1 and the guidewire lumen L3 are connected without a step inside the joint body J. Inside the joint body J, the pipeline Dt (see FIG. 18) having a crescent-shaped cross section and the inflation lumen L2' whose cross-sectional shape smoothly changes from a D-shaped cross section to a crescent-shaped cross section are connected smoothly with each other without any step therebetween along the longitudinal direction. The proximal-end portion of the inflation lumen L2' is smoothly connected to the inflation lumen L2. The cross-sectional areas of the inflation lumen L2' and the pipeline Dt from the inflation lumen L2 toward the internal space I are smaller than cross-sectional area of the inflation lumen L2.

According to the balloon catheter 10, the flow path of the fluid F that has passed through the inflation lumen L2 is narrowed by the flow path of the inflation lumen L2' and the pipeline Dt. In this case, the discharge amount of the fluid F per unit time from the opening of the pipeline Dt on the distal-end surface 3*a* toward the internal space I is suppressed. Therefore, the balloon 1 can be inflated at an appropriate speed.

According to the present embodiment, the diameter of the guidewire lumen L3 of the extension tube 4 is set to be equal to the diameter of the guidewire lumen L1 of the multi-lumen tube 2 (first example shown in FIG. 5A). However, the diameter of the extension tube 4 may be increased so as to realize a state in which the guidewire lumen L3 of the extension tube 4 has a larger diameter than the guidewire lumen L1 of the multi-lumen tube 2 (second example shown in FIG. 5B). According to such a balloon catheter 10, a part of the extension tube 4 largely invades into the U-shaped groove of the outer wall portion 3. That is, according to the second example, since the proximal-end surface 4*a* forms the step portion S2, the cross-sectional area is reduced stepwise by covering a part of the opening of the inflation lumen L2 at the position of the step portion S2. By reducing the cross section orthogonal to the axis of the core metal C1 according to the invasion amount of the extension tube 4, it is possible to make both end portions of the outer wall portion 3 in the radial direction to come in contact with the outer circumferential surface 4*b* of the extension tube 4 similar to the first example.

That is, in the second example, since the cross-sectional area of the flow path of the pipeline Dt can be further made smaller than that according to the first example, the pipeline Dt having a cross-sectional area significantly smaller than the cross-sectional area of the flow path of the inflation lumen L2 can be formed.

According to such a structure, it is possible to adjust the cross-sectional area of the pipeline Dt with respect to the cross-sectional area of the inflation lumen L2 such that it is possible to further suppress the discharge amount of the fluid F per unit time from the opening of the pipeline Dt on the distal-end surface 3*a* toward the internal space I. Therefore, it becomes easy to adjust the inflation speed of the balloon 1.

According to the present embodiment, the pipeline Dt is formed inside the first tail portion 1A, and the distal-end surface 3*a* of the outer wall portion 3 is arranged at the boundary between the first tail portion 1A and the first cone portion 1B. As a result, the velocity of the fluid F narrows the flow path immediately before being discharged into the internal space I. Since the fluid F discharged from the narrow flow path is directly filled in the internal space I without filling other space, there is little time lag between the pressurization of the fluid F and the inflation of the balloon 1.

Next, the effect of the balloon catheter 10 will be described focusing on the effect of the joint body J to which the multi-lumen tube 2, the extension tube 4, the outer wall portion 3, and the first tail portion 1A are joined.

In the joint body J, the proximal-end surface 4*a* of the extension tube 4 is end-face joint to the end surface 2*a* of the multi-lumen tube 2. Further, the outer wall portion 3 extending from the multi-lumen tube 2 is fixed at two positions on the outer circumferential portion of the proximal-end portion of the extension tube 4 along the extending direction thereof.

Therefore, the joint strength of the extension tube 4 is improved as compared with the case where the extension tube 4 is joint to the multi-lumen tube 2 only by the end surface joining between the proximal-end surface 4*a* and the end surface 2*a*. If only the end-face joining is performed, when the joint portion receives a bending moment, the stress is concentrated on the joint interface, and there is a possibility that peeling, breakage and the like may occur from a fragile portion of the joint interface.

However, according to the present embodiment, since the proximal-end portion of the extension tube 4 is also joined to the outer wall portion 3 extending from the multi-lumen tube 2, the joining area is larger than that in the case where the extension tube 4 is joined only by the end-face joining. Furthermore, since the outer wall portion 3 extends in the axial direction and is joined to the lateral side of the proximal-end portion of the extension tube 4, the moment of inertia of area is increased. Therefore, since the bending stress in the vicinity of the joint portion generated by the external force applied to the extension tube 4 is reduced, it becomes difficult for the end-face joint portion to be peeled off or damaged.

Therefore, according to the joint body J used in the balloon catheter 10 according to the present embodiment, it is also possible to improve the bending resistance of the multi-lumen tube 2 and the extension tube 4 and the joint strength at the joint portion of the multi-lumen tube 2 and the extension tube 4.

As described above, when the outer wall portion 3 is formed by the outer wall portion 3 obtained by cutting a part of the multi-lumen tube 2 for processing, there are no boundary or seam as the fragile portion is formed between the outer wall portion 3 and the multi-lumen tube 2 such that the reinforcing effect by the outer wall portion 3 is particularly large.

In the joint body J according to the present embodiment, the outer circumferential surface 1c of the first tail portion 1A of the balloon 1 is fixed to the outer circumferential portion of the outer wall portion 3 and the extension tube 4. Therefore, the joint portion between the outer wall portion 3 and the extension tube 4 is reinforced from the outer circumferential side by the first tail portion 1A.

Furthermore, according to the present embodiment, the end surface 1a of the first tail portion 1A is joint to the extension tube 4 and the multi-lumen tube 2 in a state in which the end surface 1a of the first tail portion 1A extends toward the proximal end side from the joint portion between the proximal-end surface 4a of the extension tube 4 and the end surface 2a. That is, the first tail portion 1A is joined so as to cover the end-face joint portion between the extension tube 4 and the multi-lumen tube 2 from the outer circumference.

Therefore, since the outer circumferential portion of the end-face joint portion is fixed to the inner circumferential surface 1c of the first tail portion 1A, the end-face joint portion is reinforced from the outer circumferential side.

The balloon catheter 10 is bent according to the curvature of the insertion passage at the time of being inserted into or removed from the luminal cavity. Accordingly, it is necessary for the balloon catheter 10 to have the flexibility so as to be easy to bend while having the bending resistance such that it is difficult for the kinking or the like to occur.

According to the balloon catheter 10 according to the present embodiment, the end surface 2a includes the entire distal-end surface of the partition wall portion 2B. Therefore, the proximal-end surface 4a of the extension tube 4 can be arranged in the region of the partition wall portion 2B on the end surface 2a and the region overlapping a part of the inflation lumen L2 when viewed from the axial direction.

As a result, it is easy to increase the thickness of the extension tube 4 and increase the outer diameter of the extension tube 4. Therefore, it is possible to improve the freedom degree in design for realizing the bending resistance of the extension tube 4 as required.

For example, the following designs (A) and (B) are possible.

(A) The inner diameter of the extension tube 4 can be increased without changing the wall thickness thereof so much to make the insertion of the guidewire 9 to be easy, and if necessary, it is possible to use a thicker guide wire.

(B) By increasing the wall thickness of the extension tube 4 without changing the inner diameter of the extension tube 4 so much, it is possible to suppress the bending and kinking of the extension tube 4. In this case, since the rigidity of the extension tube 4 is increased, the distal-end rigidity of the balloon catheter 10 is increased so as to achieve the effect of improving the insertability.

The designs (A) and (B) may be adopted to achieve an optimum balance, if necessary.

According to the manufacturing method for a medical balloon catheter according to the above-described embodiment, for example, the outer diameter d4 of the extension tube 4 is equal to or more than 0.4 times and equal to or less than 0.7 times of the outer diameter size d2b of the multi-lumen tube 2.

According to the present embodiment, the outer diameter of the extension tube 4 can be increased to near the value obtained by subtracting the thickness of the outer wall portion 3 from the diameter of the multi-lumen tube 2. Therefore, the outer diameter of the extension tube 4 can be made larger than that of the conventionally used extension tube.

Therefore, the freedom degree in design is increased, and it is possible to use the extension tube 4 having the insertability, the bending resistance, and the smooth guidewire insertability without increasing the diameter of the multi-lumen tube 2.

If the diameter of the extension tube 4 can be increased, the joining area in the end-face joining can be increased such that the joining strength of the end-face joint portion can be improved.

When the outer wall portion 3 extends toward the distal-end side of the first tail portion 1A, the bending resistance is also improved since the moment of inertia of area is increased by the extension tube 4 and the outer wall portion 3.

However, in a case in which there is a risk that the necessary flexibility for the extension tube 4 in the internal space I may be impaired by extending the outer wall portion 3 toward the distal-end side of the first tail portion 1A, according to the present embodiment as described above, it is more preferable that the outer wall portion 3 is formed in the range that is covered with the first tail portion 1A. In this case, since the extension tube 4 in the internal space I is flexible, it is easy for the body portion 1C of the balloon 1 to be bent. Furthermore, the portion covered by the first tail portion 1A becomes rigid due to the reinforcing effect of the outer wall portion 3 such that it becomes easy to push in the balloon catheter 10. Since it is easy to push in such a balloon catheter 10 and the body portion 1C is flexible, it has an advantage that it is easy to make the balloon catheter to reach or be inserted into the stenotic site.

According to the manufacturing method according to the present embodiment, the extension tube 4 having a larger outer diameter can be adopted as compared with the case of using other joining methods. Such an effect according to the present embodiment will be described in comparison with a first comparison example and a second comparison example.

Figure 19A:
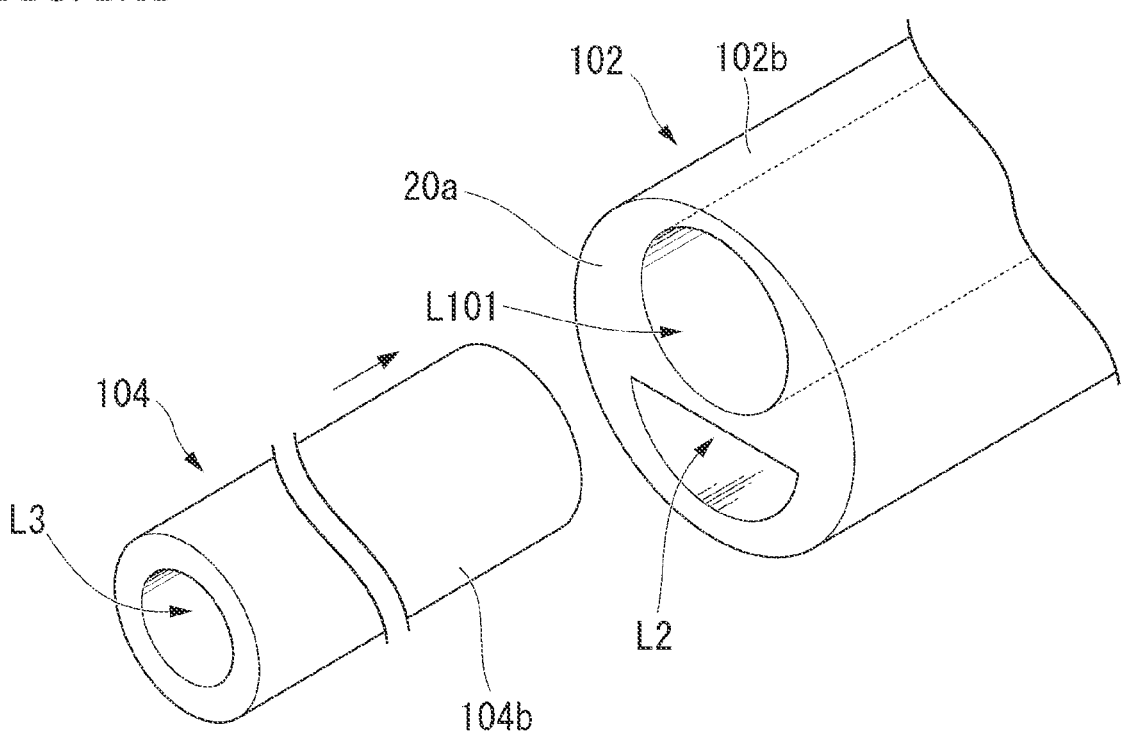
FIG. 19A is a perspective view showing a manufacturing method of a medial balloon catheter according to a first comparison example.
Figure 19B:
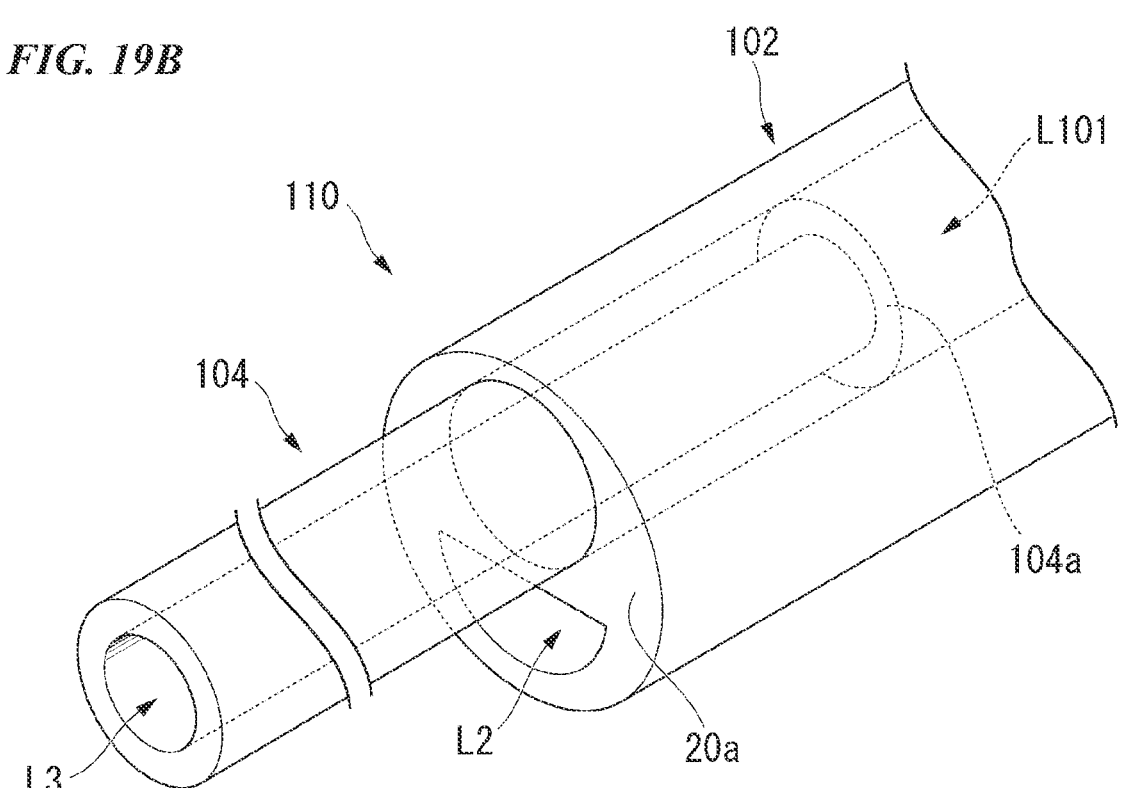
FIG. 19B is a perspective view showing the manufacturing method of the medial balloon catheter according to the first comparison example.

FIG. 19A and FIG. 19B are perspective views showing a manufacturing method of a medical balloon catheter according to the first comparison example. The same or corresponding parts as those in the present embodiment are designated by the same reference signs, and the description thereof will be omitted.

As shown in FIG. 19A, in the manufacturing method of the joined body according to the first comparison example, the multi-lumen tube 102 and the extension tube 104 are used instead of the multi-lumen tube 2 and the extension tube 4.

In the joint body according to the first comparison example, as shown in FIG. 19A and FIG. 19B, a method of inserting the extension tube 104 into the guidewire lumen L101 of the multi-lumen tube 102 is adopted. According to this comparison example, in order to make the dimensions of the guidewire lumen L3 and the inflation lumen L2 common to that according to the present embodiment, it is necessary to perform either or both of the reduction of the outer diameter of the outer circumferential surface 104*b* of the extension tube 104 and the enlargement of the outer diameter of the outer circumferential surface 102*b* of the multi-lumen tube 102. Therefore, it is possible that either or both of the buckling due to the reduction of the diameter of the extension tube 104 and the decrease of the insertability due to the increase in the diameter of the multi-lumen tube 102 may occur.

It is conceivable to narrow the cross-sectional area of the flow path of the inflation lumen L2 over the entire axial direction; however, in this case, it becomes difficult to rapidly inflate the stenotic site.

Figure 20A:
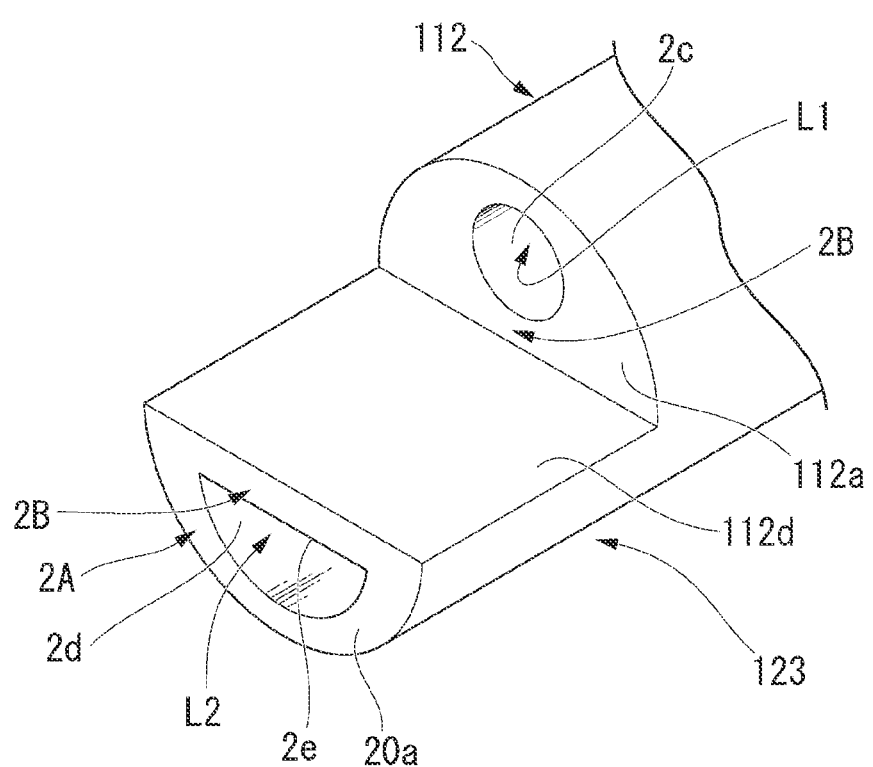
FIG. 20A is a perspective view showing a manufacturing method of a medial balloon catheter according to a second comparison example.
Figure 20B:
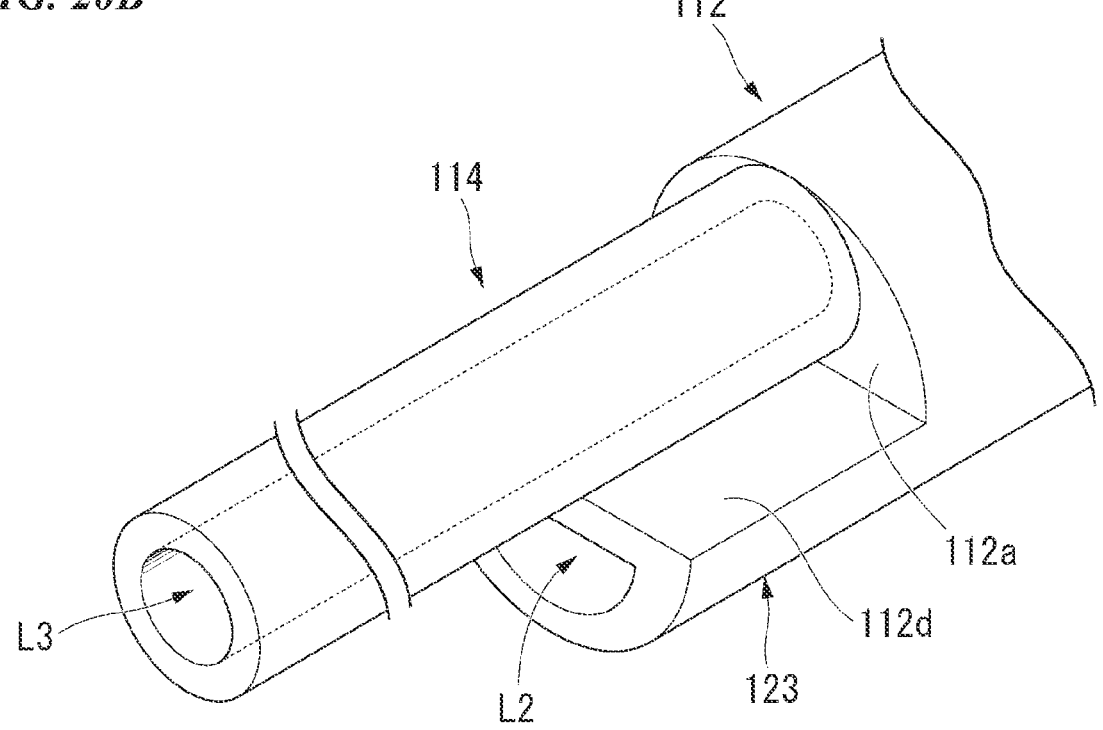
FIG. 20B is a perspective view showing the manufacturing method of the medial balloon catheter according to the second comparison example.

FIG. 20A and FIG. 20B are perspective views showing a manufacturing method of a medical balloon catheter according to a second comparison example.

In the manufacturing method of the joint body according to the second comparison example, as shown in FIG. 20A and FIG. 20B, the multi-lumen tube 112 and the extension tube 114 (see FIG. 20B) are used instead of the multi-lumen tube 2 and the extension tube 4.

In this comparison example, the multi-lumen tube 112 has a tubular protrusion 123 through which an inflation lumen L2 having a D-shaped (substantially semicircular) cross section orthogonal to the longitudinal direction penetrates inside thereof instead of the plate-shaped outer wall portion 3 having the U-shaped cross section orthogonal to the longitudinal direction as shown in the present embodiment. For example, the tubular protrusion 123 is formed by removing the distal-end portion of the multi-lumen tube 112 while leaving a part of the partition wall portion 2B covering the inflation lumen L2.

In the present comparison example, since the tubular protrusion 123 has a base portion 112*d*, it is necessary that the end surface 112*a* is narrower than the end surface 2*a* according to the present embodiment and the outer diameter of the extension tube 114 is smaller than the outer diameter of the extension tube 4. Therefore, the bending resistance of the extension tube 114 is lower than that of the extension tube 4.

In order to increase the bending resistance by increasing the outer diameter of the extension tube 114, it is necessary to narrow the cross-sectional area of the flow path of the inflation lumen L2 over the entire axial direction as in the first comparison example such that it is difficult to rapidly inflate the stenosis site.

Hereinafter, various modification examples of the medical balloon catheter and the manufacturing method thereof according to the embodiment will be described focusing on the differences from the above-described embodiment. In each modification example, the same or corresponding members as those in the above-described embodiment are designated by the same reference signs, and common description will be omitted.

First Modification Example

Figure 21:
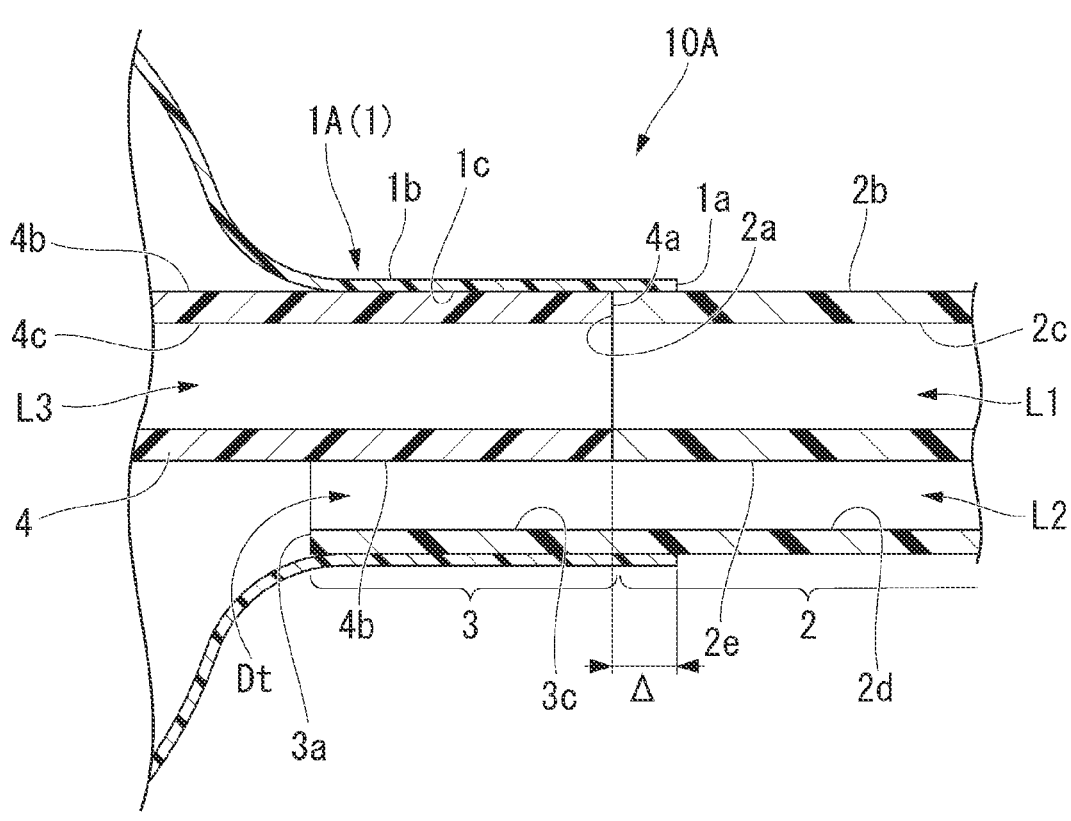
FIG. 21 is a schematic partial cross-sectional view showing an example of a cross sectional along an axial direction of a main portion of a medical balloon catheter according to a modification example (first modification example) of the embodiment of the present disclosure.

FIG. 21 is a schematic partial cross-sectional view showing an example of an axial cross section of a main portion of a medical balloon catheter according to a modification example (first modification example) of the embodiment of the present disclosure.

As shown in FIG. 21, in a balloon catheter 10A (medical balloon catheter) of the first modification example, the proximal-end surface 4*a* of the extension tube 4 and the end surface 2*a* of the multi-lumen tube 2 are joined at a position with a distance Δ at the distal-end side with respect to the end surface 1*a* of the first tail portion 1A. That is, the joint surface between the proximal-end surface 4*a* of the extension tube 4 and the end surface 2*a* of the multi-lumen tube 2 is located inside the first tail portion 1A of the balloon 1.

In the present modification example, the first tail portion 1A covers a part of the outer circumferential portion of the proximal-end portion of the extension tube 4 and the outer wall portion 3. Further, in the present modification example, the first tail portion 1A covers the joint portion between the proximal-end surface 4*a* and the end surface 2*a* and the distal-end portion of the multi-lumen tube 2.

In the present modification example, since the first tail portion 1A covers the joint portion formed by the end-face joining, the joint portion between the proximal-end surface 4*a* and the end surface 2*a* is protected by the first tail portion 1A. Therefore, the joint strength of the joint portion is further increased.

Further, in the present modification example, the outer diameter of the first tail portion 1A of the balloon 1 is larger than the outer diameter of the multi-lumen tube 2. With this configuration, when the outer wall portion 3 is inserted into the first tail portion 1A of the balloon 1, it is not necessary to bend the outer wall portion 3 such that the operability is good.

In this case, since the arrangement accuracy of the balloon 1 in the axial direction during the balloon fixing step can be relaxed, the balloon fixing step can be performed quickly.

In the present modification example, when the same heat fusion as in the embodiment is used when fixing the first tail portion 1A to the extension tube 4 and the outer wall portion 3, the outer diameter of the first tail portion 1A is decreased to the same outer diameter of the multi-lumen tube 2 similar to the embodiment.

However, in a case in which the first tail portion 1A is fixed to the outer wall portion 3 and the multi-lumen tube 2 without decreasing the diameter of the first tail portion 1A, the outer diameter of the first tail portion 1A may be larger than the outer diameter of the multi-lumen tube 2.

Second to Fourth Modification Examples

The second to fourth modification examples disclose variations of the multi-lumen tube for processing that can be used in the manufacturing method of a medical balloon catheter according to the embodiment of the present disclosure. Hereinafter, the different points from the embodiment will be mainly described.

Figures 22A, 22B, 22C:
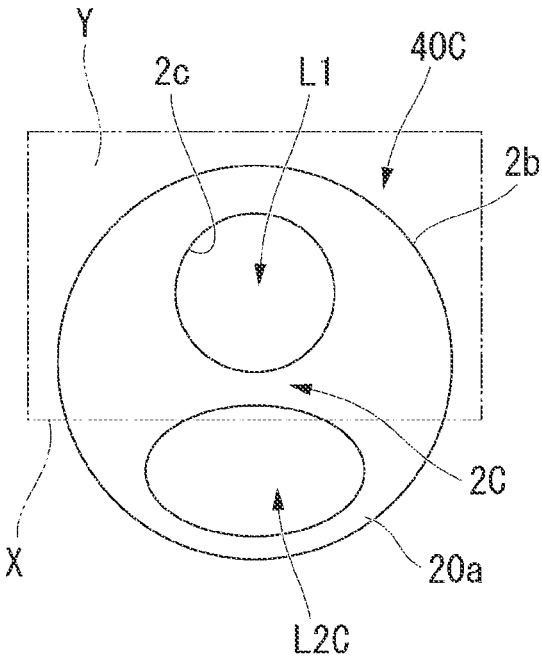
FIG. 22A is a schematic sideview showing an example of a multi-lumen tube for processing used in the manufacturing method of a medical balloon catheter according to a second modification example of the embodiment of the present disclosure.
FIG. 22B is a schematic sideview showing an example of a multi-lumen tube for processing used in the manufacturing method of a medical balloon catheter according to a third modification example of the embodiment of the present disclosure.
FIG. 22C is a schematic sideview showing an example of a multi-lumen tube for processing used in the manufacturing method of a medical balloon catheter according to a fourth modification example of the embodiment of the present disclosure.
Figure 23:
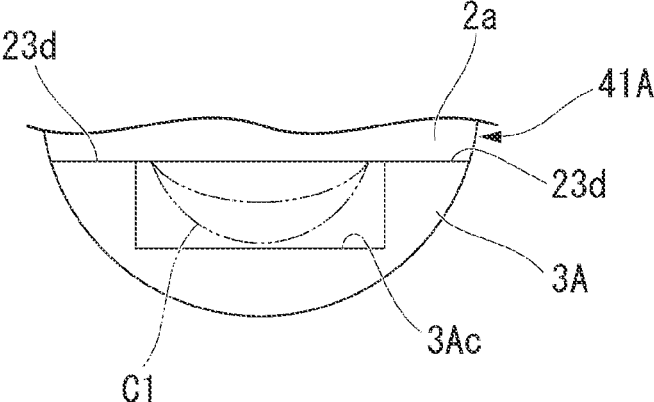
FIG. 23 is a schematic cross-sectional view showing an example of a manufacturing method of a medical balloon catheter according to a modification example (second modification example) of the embodiment of the present disclosure.

FIG. 22A to FIG. 22C are schematic side views showing examples of multi-lumen tubes for processing used in manufacturing methods of a medical balloon catheter according to the modification examples (second to fourth modification examples) of the embodiment of the present disclosure. FIG. 23 is a schematic cross-sectional view showing an example of a manufacturing method of a medical balloon catheter according to the modification example (second modification example) of the embodiment of the present disclosure.

In the second modification, a multi-lumen tube 40A for processing as shown in FIG. 22A is used instead of the multi-lumen tube 2 for processing.

The multi-lumen tube 40A includes an inflation lumen L2A (second lumen) having a rectangular cross section orthogonal to the axial direction instead of the inflation lumen L2.

In the outer wall portion forming step of the present modification example, similar to the present embodiment, the distal-end portion of the multi-lumen tube 40A is removed by the radial cut plane Y and the axial cut plane X so as to remove the entire partition wall portion 2B including the flat surface portion 2e.

As a result, the multi-lumen tube 41A having the outer wall portion 3A as shown in FIG. 23 is formed instead of the outer wall portion 3.

The outer wall portion 3A includes a square groove-shaped inner circumferential surface 3Ac that opens between the end surface 23d and the end surface 23d and extends in the axial direction, instead of the U-shaped inner circumferential surface 3c according to the embodiment.

The inner circumferential surface 3Ac is deformed so as to form a part of the inner circumferential surface of the crescent-shaped pipeline Dt by being heat-sealed using the core metal C1 similar to that according to the embodiment. The cross-sectional shape of the core metal C1 only has to be a cross-sectional shape that is insertable into the inflation lumen L2A and is not limited to the substantially semicircular shape or the crescent shape.

According to the third modification example, a multi-lumen tube 40B for processing as shown in FIG. 22B is used instead of the multi-lumen tube 2 for processing.

The multi-lumen tube 40B includes an inflation lumen L2B (second lumen) having a triangular cross section orthogonal to the axis instead of the inflation lumen L2. For example, the shape of the inflation lumen L2B in the cross section orthogonal to the axis is an isosceles triangle having the flat surface portion 2e as the base side and the apex on the opposite side to the partition wall portion 2B.

In the outer wall portion forming step according to the present modification example, the distal-end portion of the multi-lumen tube 40B for processing is removed by the cut plane Y and the cut plane X so as to remove the entire partition wall portion 2B including the flat surface portion 2e.

As a result, although not particularly shown in figures, an outer wall portion having a V-shaped groove-shaped inner circumferential surface is formed instead of the inner circumferential surface 3c of the outer wall portion 3.

In the fourth modification example, a multi-lumen tube 40C for processing as shown in FIG. 22C is used instead of the multi-lumen tube 2 for processing.

The multi-lumen tube 40C includes an inflation lumen L2C (second lumen) having an elliptical cross section orthogonal to the axis instead of the inflation lumen L2. When viewed from the axial direction, a partition wall portion 2C surrounded by an ellipse and an arc is formed between the inflation lumen L2C and the guidewire lumen L1.

In the outer wall portion forming step according to the present modification example, the distal-end portion of the multi-lumen tube 40C is removed by the cut plane Y and the cut plane X. Here, the position of the cut plane X is set to a position crossing the inflation lumen L2C such that an opening is formed in a part of the inflation lumen L2C covered by the partition wall portion 2C.

As a result, although not particularly shown in figures, an outer wall portion having a C-shaped groove-shaped inner circumferential surface is formed instead of the inner circumferential surface 3c of the outer wall portion 3.

Fifth and Sixth Modification Examples

Figures 24A, 24B:
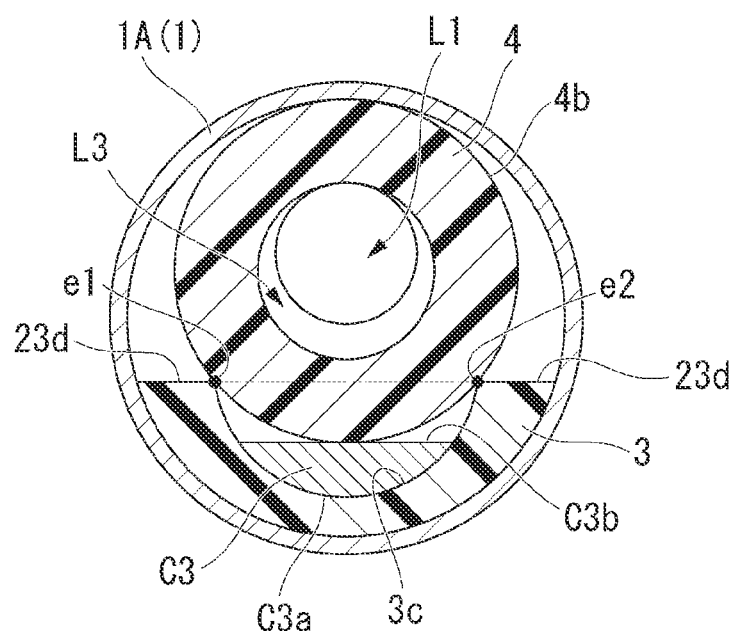
FIG. 24A is a schematic cross-sectional view showing an example of a manufacturing method of a medical balloon catheter according to a modification example (fifth modification example) of the embodiment of the present disclosure.
FIG. 24B is a schematic cross-sectional view showing an example of a manufacturing method of a medical balloon catheter according to a modification example (sixth modification example) of the embodiment of the present disclosure.

FIG. 24A and FIG. 24B are schematic cross-sectional views showing examples of a manufacturing method of a medical balloon catheter according to modification examples (fifth and sixth modification example) of the embodiment of the present disclosure.

Figure 25:
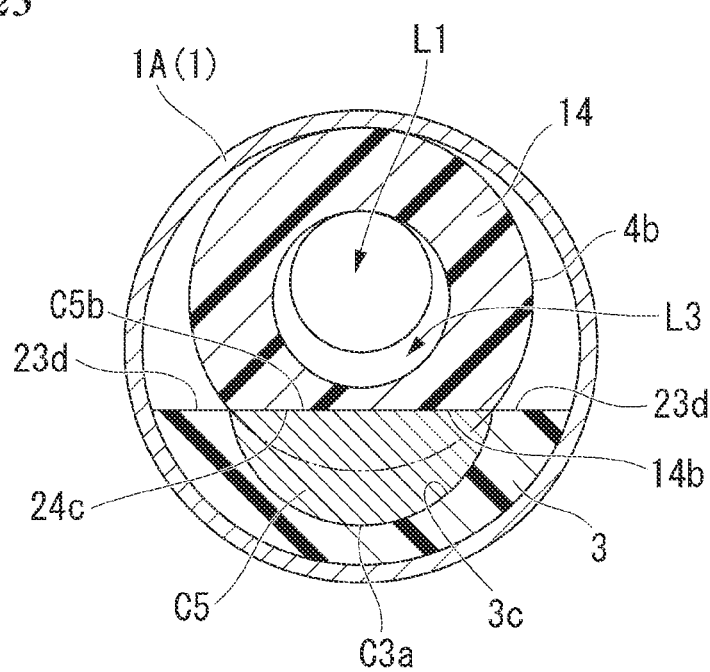
FIG. 25 is a schematic cross-sectional view showing an example of a manufacturing method of a medical balloon catheter according to a modification example (seventh modification example) of the embodiment of the present disclosure.
Figure 26:
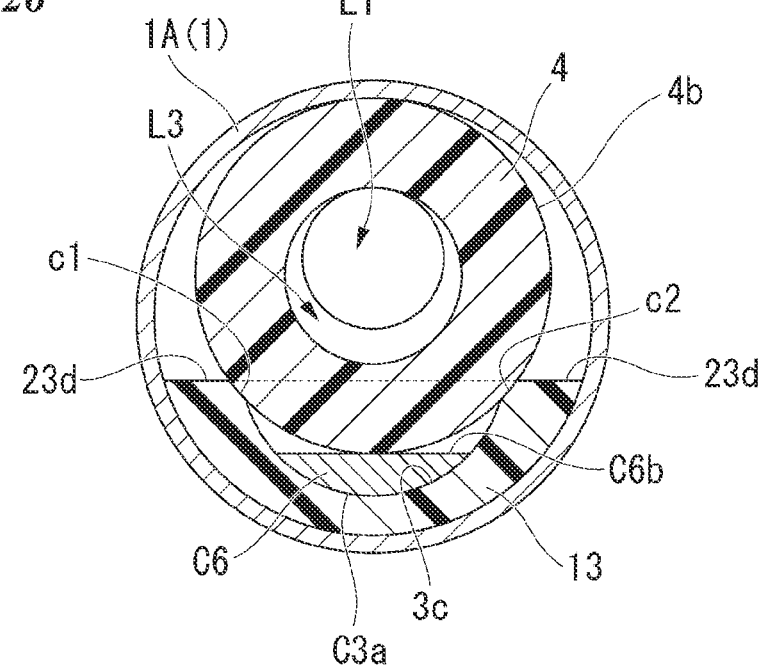
FIG. 26 is a schematic cross-sectional view showing an example of a manufacturing method of a medical balloon catheter according to a modification example (eighth modification example) of the embodiment of the present disclosure.
Figure 27:
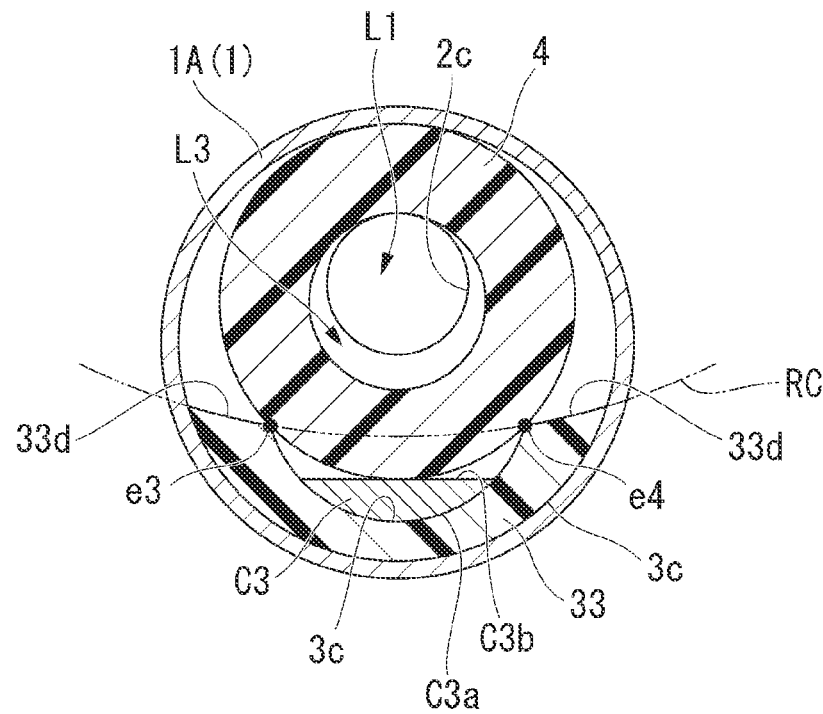
FIG. 27 is a schematic cross-sectional view showing an example of a manufacturing method of a medical balloon catheter according to a modification example (ninth modification example) of the embodiment of the present disclosure.

However, FIG. 24A and FIG. 24B show the arrangement before the heat fusion similar to FIG. 4C. In FIG. 24A and FIG. 24B, as an example, the inner diameter of the guidewire lumen L3 is larger than the inner diameter of the guidewire lumen L1; however, the guidewire lumen L1 and the guidewire lumen L3 may have the same diameter similar to the first example according to the embodiment. The same configuration is applied to FIG. 25 to FIG. 27 shown below.

As shown in FIG. 24A and FIG. 24B, in the fifth and sixth modification examples, when the multi-lumen tube 2 and the outer wall portion 3 are inserted into the first tail portion 1A, the inner edge portion e1 and inner edge portion e2 of the end surface 23d as the edge portions of the outer wall portion 3 abut to and come in contact with the outer circumferential surface 4b of the extension tube 4.

In the manufacturing method according to the fifth modification, the core metal C3 is used instead of the core metal C1 according to the present embodiment. The core metal C3 has a D-shaped cross section orthogonal to the longitudinal direction, and includes a convex surface portion C3a and a flat surface portion C3b. The cross-sectional shape of the core metal C3 is such that the flat surface portion C3b and the outer circumferential surface 4b are in contact with each other and the convex surface portion C3a substantially follows the inner circumferential surface 3c of the outer wall portion 3 in a state in which the outer circumferential surface 4b is in contact with the edge portion e1 and the edge portion e2.

According to the present modification example, the misalignment of the extension tube 4 is suppressed during the insertion into the first tail portion 1A and the fixing step.

In the manufacturing method according to the sixth modification example, as shown in FIG. 24B, a core metal C4 having a crescent-shaped cross section is used instead of the core metal C3 having a D-shaped cross section according to the fifth modification example. The core metal C4 has a crescent shape that substantially fills the space between the outer circumferential surface 4b and the inner circumferential surface 3c in a state in which the outer circumferential surface 4b is in contact with the edge portion e1 and the edge portion e2. The core metal C4 includes a cylindrical concave surface portion C4b substantially along the outer circumferential surface 4b and a cylindrical convex surface portion C4a substantially along the inner circumferential surface 3c.

According to the present modification example, the position of the extension tube 4 can be regulated not only by the edge portion e1 and the edge portion e2 but also by the concave surface portion C4b of the core metal C4 such that the misalignment of the extension tube 4 in the radial direction is further suppressed at the time of placing the extension tube 4 to the outer wall portion 3.

Seventh Modification Example

FIG. 25 is a schematic cross-sectional view showing an example of a manufacturing method of a medical balloon catheter according to a modification example (seventh modification example) according to the embodiment of the present disclosure.

As shown in FIG. 25, in this modification example, the extension tube 14 is used instead of the extension tube 4. The extension tube 14 is characterized in that the cross section seen from the axial direction is not circular but in a shape formed by a straight line and an arc at least in the range facing the outer wall portion 3 in the radial direction. That is, a flat surface portion 14b extending in the axial direction on the outer circumferential portion facing the outer wall portion 3 is formed in the extension tube 14.

In the present modification example, instead of the flat surface portion C3b of the core metal C3, the core metal C5 having the flat surface portion C5b on which the flat surface portion 14b of the extension tube 14 can be placed is used. In FIG. 25, the flat surface portion C5b is described so as to be on the same plane as the end surface 23d; however, the flat surface portion C5b may be in contact with the flat surface portion 14b inside the U-shaped groove of the outer wall portion 3.

According to the present modification example, since the extension tube 14 is placed on the flat surface portion C5b with the flat surface portion 14b of the extension tube 14 facing to the flat surface portion C5b, the extension tube 14 can be stably placed.

Eighth Modification Example

FIG. 26 is a schematic cross-sectional view showing an example of a manufacturing method of a medical balloon catheter according to a modification example (eighth modification example) according to the embodiment of the present disclosure.

As shown in FIG. 26, the present modification example is characterized in that the side of the outer wall portion in contact with the extension tube 4 is chamfered.

In the outer wall portion forming step of the present modification example, the outer wall portion 13 is formed instead of the outer wall portion 3. The outer wall portion 13 has the chamfered portion c1 and the chamfered portion c2 formed on the inner edge portion of each end surface 23d.

In the present modification example, the core metal C6 is used instead of the core metal C3 according to the fifth modification example. The core metal C6 has the same cross-sectional shape as that of the core metal C3 except that the core metal C6 includes a flat surface portion C6b instead of the flat surface portion C3b, wherein the flat surface portion C6b comes into contact with the outer circumferential surface 4b in a state in which the chamfered portion c1 and the chamfered portion c2 are in contact with the outer circumferential surface 4b.

According to the present modification example, the extension tube 4 is placed on the outer wall portion 13 in a state of being locked to the chamfered portion c1 and the chamfered portion c2 that are wider than the edge portion e1 and the edge portion e2 such that the misalignment of the extension tube 4 in the radial direction when the extension tube 4 is placed thereto is suppressed.

Ninth Modification Example

The ninth modification example is a variation of the shape of the outer wall portion.

FIG. 27 is a schematic cross-sectional view showing an example of a manufacturing method of a medical balloon catheter according to a modification example (ninth modification example) according to the embodiment of the present disclosure.

As shown in FIG. 27, in the manufacturing method according to the ninth modification, in the outer wall portion forming step, the outer wall portion 33 having an inclination surface 33d is used instead of each end surface 23d of the outer wall portions 3 that are located on the same plane as each other.

Each inclination surface 33d is inclined toward the central portion in the circumferential direction of the inner circumferential surface 3c from the outer circumferential surface 3b (outer circumferential portion) toward the inner circumferential surface 3c. Each inclination surface 33d may be flat or non-planar. In the example shown in FIG. 27, each inclination surface 33d is a concave curved surface along an arc RC having a curvature radius larger than that of the outer circumferential surface 3b in a cross section orthogonal to the axis.

The edge portion e3 and the edge portion e4 are formed at the intersection portion of each inclination surface 33d and the inner circumferential surface 3c.

The shape of the cross section orthogonal to the axis of the core metal may be D-shaped (semi-circular) or crescent-shaped. In the example shown in FIG. 27, the core metal C3 in which the position of the flat surface portion C3b is changed according to the position of the outer circumferential surface 4b is used.

According to the present modification, each inclination surface 33d is inclined so as to open outward from the edge portion e3 and the edge portion e4, respectively. Therefore, the extension tube 4 is placed thereto in a state where each inclination surface 33d faces the outer circumferential surface 4b of the extension tube 4.

Therefore, it is easy to determine the position of the extension tube 4 at the time of placing the extension tube 4.

According to the embodiment and each modification example, it has been described that the extension tube is provided with the marker M1 and the marker M2. However, the extension tube may not be provided with any marker.

In the embodiment and each modification example, an example in which the outer wall portion has a U-shaped cross section orthogonal to the axis has been described. By joining the lateral side of the outer wall portion to the outer circumferential surface of the extension tube, the inner surface of the outer wall portion and the outer circumferential surface of the extension tube are connected to form a pipeline. This pipeline is configured to communicate with the inflation lumen such that the inflation lumen is substantially extended in the distal direction by the length of the outer wall portion. As a result, the position where the fluid that inflates the balloon is discharged into the balloon is closer to the center of the balloon, which contributes to the smooth inflation of the balloon.

In this case, since a part of the end surface of the extension tube partially closes the distal-end opening of the inflation lumen of the multi-lumen tube, the cross-sectional area of the pipeline is smaller than the cross-sectional area of the inflation lumen in the multi-lumen. Therefore, since the flow path of the fluid that has passed through the inflation lumen is narrowed in the pipeline, the flow velocity in the pipeline is increased, and the balloon can be inflated quickly.

Also, the outer wall portion is a plate-shaped member having a groove (for example, a U-shaped groove) along the longitudinal direction, and only a part of the extension tube enters the internal space of the groove. Therefore, for example, the diameter of the extension tube can be increased as compared with the case in which the multi-lumen tube as shown in the second comparison example has a tubular protrusion at the distal-end side thereof. Therefore, it is possible to suppress the kinking of the extension tube while increasing the joint strength between the extension tube and the multi-lumen tube. Since the strength of the balloon catheter is increased in this manner, the freedom degree in design of the balloon catheter can be widened.

Although the preferred embodiments of the present invention have been described above, the present invention is not limited to these embodiments. Configurations can be added, omitted, replaced, and other modifications without departing from the scope of the present invention.

Further, the present invention is not limited by the above description, but is limited only by the appended claims.

What is claimed is:

1. A medical catheter, comprising:
a multi-lumen tube including a first lumen and a second lumen;
an extension tube fixed to a first end surface in a longitudinal direction of the multi-lumen tube, extending from the first end surface along the longitudinal direction, and including a third lumen communicating with the first lumen; and
an outer wall portion extending from the multi-lumen tube along the extension tube and configured to cover a part of an outer surface of the extension tube, the outer wall portion including a pipeline formed to communicate with the second lumen and having a part of the outer surface in an inner surface of the pipeline: and
a balloon fixed to at least one of the multi-lumen tube, the extension tube, and the outer wall portion,
wherein the outer wall portion having second and third end surfaces each extending in the longitudinal direction and each directly contacting the outer surface of the extension tube,
an internal space of the balloon is formed to surround the extension tube and the internal space communicates with the second lumen through the pipeline, and
the balloon includes a proximal-end tail fixed to at least the outer wall portion, and a distal end of the outer wall portion is disposed at an inner side of the proximal-end tail.

2. The medical catheter according to claim 1, wherein the outer wall portion is formed of a same material as a side wall portion along the second lumen in the multi-lumen tube.

3. The medical catheter according to claim 1,
wherein the first lumen and the third lumen are configured such that a guidewire is insertable through the first lumen or the third lumen, and the second lumen is configured for introducing liquid for inflating the balloon into the internal space.

4. The medical catheter according to claim 1, wherein an outer diameter of the extension tube is equal to or larger than 0.4 times and equal to or less than 0.7 times of an outer diameter of the multi-lumen tube.

5. The medical catheter according to claim 1, wherein a joint portion of the end surface and the extension tube is disposed at the inner side of the proximal-end tail.

6. The medical catheter according to claim 1, wherein the outer wall portion is a plate-shaped protrusion having a substantial U-shaped cross section that is orthogonal to the longitudinal direction.

7. The medical catheter according to claim 1,
wherein the extension tube includes an end portion facing the first end surface, and
a side surface of the end portion of the extension tube is in direct contact with lateral sides extending in the longitudinal direction on the second end surface of the outer wall portion.

8. The medical catheter according to claim 1, wherein a proximal-end surface of the extension tube comes into contact with the first end surface.

9. The medical catheter according to claim 1, wherein part of the extension tube is disposed so as to intrude into an inner side of the outer wall portion.

10. The medical catheter according to claim 1, wherein a proximal-end surface of the extension tube is configured to form a step portion which is in contact with the first end surface in a stepped shape.

11. The medical catheter according to claim 1, wherein a cross-sectional area orthogonal to the longitudinal direction in the second lumen at a distal-end side is smaller than that at a proximal-end side.

12. The medical catheter according to claim 1, wherein a cross section orthogonal to the longitudinal direction in the second lumen is in a crescent shape at least at a distal end side.

13. The medical catheter according to claim 1, wherein the pipeline is configured to eject liquid for inflating the balloon from the second lumen into the balloon to inflate the balloon.

14. The medical catheter according to claim 1, wherein a cross section orthogonal to the longitudinal direction in the second lumen is in an elliptic shape.

* * * * *